(12) United States Patent
Pearson et al.

(10) Patent No.: US 6,790,834 B1
(45) Date of Patent: *Sep. 14, 2004

(54) CYTOSTATIC AGENTS

(75) Inventors: Lindsey Ann Pearson, Oxford (GB); Andrew Paul Ayscough, Oxford (GB); Philip Huxley, Oxford (GB); Alan Drummond, Oxford (GB)

(73) Assignee: British Biotech Pharmaceuticals, Ltd., Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/514,083

(22) Filed: Feb. 28, 2000

Related U.S. Application Data

(62) Division of application No. 08/925,584, filed on Sep. 8, 1997, now Pat. No. 6,169,075.

(30) Foreign Application Priority Data

Sep. 10, 1996 (GB) .............................................. 9618899
Jun. 24, 1997 (GB) .............................................. 9713202
Mar. 12, 1998 (WO) .............................. PCT/GB98/00754

(51) Int. Cl.$^7$ ................................................. C07K 5/06
(52) U.S. Cl. ...................... 514/19; 514/575; 562/445; 562/553
(58) Field of Search .................. 514/19, 575; 562/445, 562/553

(56) References Cited

U.S. PATENT DOCUMENTS 5,872,152 A    2/1999 Brown et al. ............... 514/575

OTHER PUBLICATIONS

Viallet, Lung Cancer 15 (3) 367–73, 1996.*
Kemeny, Seminars in Oncology 21 (4 Suppl 7) 67–75, 1994.*
Newton, Expert Opinion on Investigational Drugs 9 (12) 2815–29, 2000.*
Giese, Journal of Cancer Research and Clinical Oncology 127 (4) 217–25, 2001.*
Garattini, European Journal of Cancer 37 Suppl 8 S128–47, 2001.*
Ragnhammar, Acta Oncologica 40 (2–3) 282–308, 2001.*

* cited by examiner

*Primary Examiner*—Christopher S. F. Low
*Assistant Examiner*—David Lukton
(74) *Attorney, Agent, or Firm*—Greenberg Traurig LLP; Eugene C. Rzucidlo

(57) ABSTRACT

Compounds of formula I are disclosed

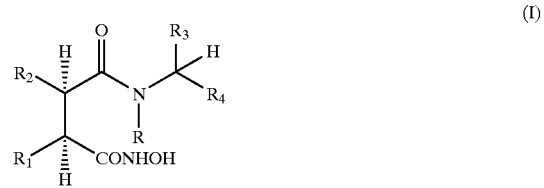

(I)

wherein $R_4$ is an ester or thioester group, and R, $R_1$, $R_2$, and $R_3$ are as defined in the specification are inhibitors of rapidly dividing tumor cells.

46 Claims, No Drawings

CYTOSTATIC AGENTS

This application is a divisional of application Ser. No. 08/925,584, filed Sep. 8, 1997, now U.S. Pat. No. 6,169,075 which claims priority to applications GB 9618899.0 filed Sep. 10, 1996 and GB 9713202.1, filed Jun. 24, 1997.

The present invention relates to therapeutically active esters and thioesters, to processes for their preparation, to pharmaceutical compositions containing them, and to the use of such compounds in medicine. In particular, the compounds are inhibitors of the proliferation of a range of rapidly dividing tumour cells, for example melanoma and/or lymphoma cells.

BACKGROUND TO THE INVENTION

1. Anti-Proliferative Agents

There is a need in cancer therapy for therapeutic compounds which are inhibitors of the proliferation of tumour cells. One compound which is known to have such activity is 5-fluorouracil (5-FU).

2. Anti-Metastatic and Anti-Invasive Agents

Compounds which have the property of inhibiting the action of the metalloproteinase enzymes involved in connective tissue breakdown and remodelling, such as fibroblast collagenase (Type 1), PMN-collagenase, 72 kDa-gelatinase, 92 kDa-gelatinase, stromelysin, stromelysin-2 and PUMP-1 (known as "matrix metalloproteinases", and herein referred to as MMPs) have been proposed and are being tested in the clinic for the treatment of solid tumours. Cancer cells are particularly adept at utilising the MMPs to achieve rapid remodelling of the extracellular matrix, thereby providing space for tumour expansion and permitting metastasis. MMP inhibitors should minimise these processes and thus slow or prevent cancer progression.

A known class of MMP inhibitors having a hydroxamic acid group as the zinc binding group may be represented by the structural formula (IA)

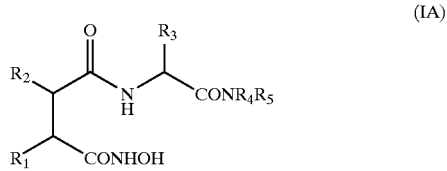

(IA)

in which the groups $R_1$ to $R_6$ are variable in accordance with specific prior art disclosures of such compounds. Examples of patent publications disclosing MMP inhibitors of formula (IA) are:

| | |
|---|---|
| U.S. Pat. No. 4599361 | (Searle) |
| EP-A-2321081 | (ICI) |
| EP-A-0236872 | (Roche) |
| EP-A-0274453 | (Bellon) |
| WO 90/05716 | (British Biotech) |
| WO 90/05719 | (British Biotech) |
| WO 91/02716 | (British Biotech) |
| WO 92/09563 | (Glycomed) |
| U.S. Pat. No. 5183900 | (Glycomed) |
| U.S. Pat. No. 5270326 | (Glycomed) |
| WO 92/17460 | (SB) |
| EP-A-0489577 | (Celltech) |
| EP-A-0489579 | (Celltech) |
| EP-A-0497192 | (Roche) |
| U.S. Pat. No. 5256657 | (Sterling) |
| WO 92/13831 | (British Biotech) |
| WO 92/22523 | (Research Corp) |
| WO 93/09090 | (Yamanouchi) |
| WO 93/09097 | (Sankyo) |
| WO 93/20047 | (British Biotech) |
| WO 93/24449 | (Celltech) |
| WO 93/24475 | (Celltech) |
| EP-A-0574758 | (Roche) |
| EP-A-0575844 | (Roche) |
| WO 94/02446 | (British Biotech) |
| WO 94/02447 | (British Biotech) |
| WO 94/21612 | (Otsuka) |
| WO 94/21625 | (British Biotech) |
| WO 94/24140 | (British Biotech) |
| WO 94/25434 | (Celltech) |
| WO 94/25435 | (Celltech) |
| WO 95/04033 | (Celltech) |
| WO 95/04735 | (Syntex) |
| WO 95/04715 | (Kanebo) |
| WO 95/06031 | (Immunex) |
| WO 95/09841 | (British Biotech) |
| WO 95/12603 | (Syntex) |
| WO 95/19956 | (British Biotech) |
| WO 95/19957 | (British Biotech) |
| WO 95/19961 | (British Biotech) |
| WO 95/19965 | (Glycomed) |
| WO 95/22966 | (Sanofi Winthrop) |
| WO 95/23790 | (SB) |

BRIEF DESCRIPTION OF THE INVENTION

This invention is based on the identification of a class of ester and thioester compounds which inhibit proliferation of rapidly dividing cells. The ester and thioester compounds in question have certain structural similarities to known MMP inhibitors of general formula (IA) above disclosed in the foregoing patent publications. However, instead of the amide group —$CONR_4R_5$ of formula (IA), they have an ester or thioester group. Despite the similarity of structure, it has been shown that compounds of the invention which have little or no MMP inhibitory activity are nonetheless potent inhibitors of such cell proliferation, implying a novel mechanism is at work. This antiproliferation property suggests a utility for the compounds of the present invention in the treatment of cancers.

Although the patent publications listed above predominantly disclose MMP inhibiting compounds of formula (IA), ie having an amide group —$CONR_4R_5$, a few (WO 92/09563, U.S. Pat. No. 5,183,900, U.S. Pat. No. 5,270,326, EP-A-0489577, EP-A-0489579, WO 93/09097, WO 93/24449, WO 94/25434, WO 94/25435, WO 95/04033, WO 95/19965, and WO 95/22966) include within their generic disclosure compounds having a carboxylate ester group in place of the amide group. The carboxylate ester compounds with which this invention is concerned thus represent a selection of a notional subclass from the compounds proposed in the art as MMP inhibitors, for a specific and previously unrecognised pharmaceutical utility.

WO 95/04033 discloses $N^4$-hydroxy-$N^1$-(1-(S)-methoxycarbonyl-2,2-dimethylpropyl)-2-(R)-(4-chlorophenylpropyl)succinamide as an intermediate for the preparation of the corresponding methylamide MMP inhibitor. In addition, *Int. J. Pept. Protein Res.* (1996), 48(2), 148–155 discloses the compound

Ph-CH$_2$CH(CO-lle-OtBu)CH$_2$CONHOH as an intermediate in the preparation of compounds which are inhibitors of neurotensin-degrading enzymes. However, those two appear to be the only specific known carboxylate ester compounds of the kind with which this invention is concerned.

The present inventors' findings of inhibition of proliferation of rapidly dividing cells, including such tumour cells as lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma or endothelioma cells, by the esters and thioesters of the present invention, by a mechanism other than MMP inhibition, is not disclosed in or predictable from those earlier publications.

DETAILED DESCRIPTION OF THE INVENTION

In its broadest aspect, the present invention provides a method for inhibiting proliferation of tumour cells in mammals, comprising administering to the mammal suffering such proliferation an amount of a compound of general formula (I) or a pharmaceutically acceptable salt hydrate or solvate thereof sufficient to inhibit such proliferation:

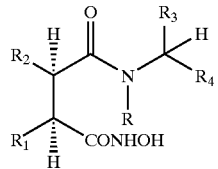

(I)

wherein
R is hydrogen or $(C_1-C_6)$alkyl;
$R_1$ is hydrogen;
$(C_1-C_6)$alkyl;
$(C_2-C_6)$alkenyl;
phenyl or substituted phenyl;
phenyl $(C_1-C_6)$alkyl or substituted phenyl$(C_1-C_6)$alkyl;
phenyl $(C_2-C_6)$alkenyl or substituted phenyl$(C_2-C_6)$ alkenyl
heterocyclyl or substituted heterocyclyl;
heterocyclyl$(C_1-C_6)$alkyl or substituted heterocyclyl$(C_1-C_6)$alkyl;
a group $BSO_nA$— wherein n is 0, 1 or 2 and B is hydrogen or a $(C_1-C_6)$ alkyl, phenyl, substituted phenyl, heterocyclyl substituted heterocyclyl, $(C_1-C_6)$acyl, phenacyl or substituted phenacyl group, and A represents $(C_1-C_6)$alkylene;
hydroxy or $(C_1-C_6)$alkoxy;
amino, protected amino, acylamino, $(C_1-C_6)$alkylamino or di-$(C_1-C_6)$alkylamino;
mercapto or $(C_1-C_6)$alkylthio;
amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$ alkyl, mercapto$(C_1-C_6)$alkyl or carboxy$(C_1-C_6)$ alkyl wherein the amino-, hydroxy-, mercapto- or carboxyl- group are optionally protected or the carboxyl-group amidated;
lower alkyl substituted by carbamoyl, mono(lower alkyl) carbamoyl, di(lower alkyl)carbamoyl, di(lower alkyl) amino, or carboxy-lower alkanoylamino; or
a cycloalky, cycloalkenyl or non-aromatic heterocyclic ring containing up to 3 heteroatoms, any of which may be (i) substituted by one or more substituents selected from $C_1-C_6$ alkyl, $C_2-C_6$ alkenyl, halo, cyano (—CN), —$CO_2H$, —$CO_2R$, —$CONH_2$, —CONHR, —$CON(R)_2$, —OH, —OR, oxo—, —SH, —SR, —NHCOR, and —$NHCO_2R$ wherein R is $C_1-C_6$ alkyl or benzyl and/or (ii) fused to a cycloalkyl or heterocyclic ring;

$R_2$
is a $C_1-C_{12}$ alkyl,
$C_2-C_{12}$ alkenyl,
$C_2-C_{12}$ alkynyl,
phenyl($C_1-C_6$ alkyl)-,
heteroaryl($C_1-C_6$ alkyl)-,
phenyl($C_2-C_6$ alkenyl)-,
heteroaryl($C_2-C_6$ alkenyl)-,
phenyl($C_2-C_6$ alkynyl)-,
heteroaryl($C_2-C_6$ alkynyl)-,
cycloalkyl($C_1-C_6$ alkyl)-,
cycloalkyl($C_2-C_6$ alkenyl)-,
cycloalkyl($C_2-C_6$ alkynyl)-,
cycloalkenyl($C_1-C_6$ alkyl)-,
cycloalkenyl($C_2-C_6$ alkenyl)-,
cycloalkenyl($C_2-C_6$ alkynyl)-,
phenyl($C_1-C_6$ alkyl)O($C_1-C_6$ alkyl)-, or
heteroaryl($C_1-C_6$ alkyl)O($C_1-C_6$ alkyl)- group,
any one of which may be optionally substituted by
$C_1-C_6$ alkyl,
$C_1-C_6$ alkoxy,
halo,
cyano (—CN),
phenyl, or
phenyl substituted by
$C_1-C_6$ alkyl,
$C_1-C_6$ alkoxy,
halo, or
cyano (—CN);

$R_3$
is the characterising group of a natural or non-natural α amino acid in which any functional groups may be protected; and $R_4$
is an ester or thioester group,
or a pharmaceutically acceptable salt, hydrate or solvate thereof.

In another broad aspect of the invention, there is provided the use of a compound of formula (I) as defined in the immediately preceding paragraph, in the preparation of a pharmaceutical composition for inhibiting proliferation of tumour cells in mammals.

The present invention also provides novel compounds of general formula (I) above wherein R, $R_1$, $R_2$, $R_3$ and $R_4$ are as defined above with reference to formula (I), and pharmaceutically acceptable salts, hydrates or solvates thereof, PROVIDED THAT:

(i) when R and $R_1$ are hydrogen, $R_2$ is 4-chlorophenylpropyl, and $R^3$ is tert-butyl, then $R_4$ is not a methyl carboxylate ester group; and (ii) when R and $R_1$ are hydrogen, $R_2$ is phenylmethyl, and $R^3$ is 1-methylprop-1-yl, then $R_4$ is not a tert-butyl carboxylate ester group.

One particular sub-group of the novel esters and thioesters of the invention consists of compounds of formula (I) above, wherein:

R, $R_1$ and $R_4$ are as defined above with reference to formula (I)

$R_2$ is $C_1$-$C_{12}$ alkyl, $C_2$-$C_{12}$ alkenyl, $C_2$-$C_{12}$ alkynyl, biphenyl($C_1$-$C_6$ alkyl)-, phenylheteroaryl($C_1$-$C_6$ alkyl)-, heteroarylphenyl($C_1$-$C_6$ alkyl)-, biphenyl($C_2$-$C_6$ alkenyl)-, phenylheteroaryl($C_2$-$C_6$ alkenyl)-, heteroarylphenyl($C_2$-$C_6$ alkenyl)-, phenyl($C_2$-$C_6$ alkynyl)-, heteroaryl($C_2$-$C_6$ alkynyl)-, biphenyl($C_2$-$C_6$ alkynyl)-, phenylheteroaryl($C_2$-$C_6$ alkynyl)-, heteroarylphenyl($C_2$-$C_6$ alkynyl)-, phenyl($C_1$-$C_6$ alkyl)O($C_1$-$C_6$ alkyl)-, or heteroaryl($C_1$-$C_6$ alkyl)O($C_1$-$C_6$ alkyl)-, any one of which may be optionally substituted on a ring carbon atom by $C_1$-$C_6$ alkyl, $C_1$-$C_6$ alkoxy, halo, or cyano (—CN); and $R_3$ is $C_1$-$C_6$ alkyl, optionally substituted benzyl, optionally substituted phenyl, optionally substituted heteroaryl; or the characterising group of a natural α amino acid, in which any functional group may be protected, any amino group may be acylated and any carboxyl group present may be amidated; or a heterocyclic($C_1$-$C_6$)alkyl group, optionally substituted in the heterocyclic ring;

and pharmaceutically acceptable salts, hydrates or solvates thereof.

As used herein the term "($C_1$-$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

The term "($C_2$-$C_6$)alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2$-$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl- 2-propynyl, 2-pentynyl, 3-pentynyl, 4-pentynyl, 2-hexynyl, 3-hexynyl, 4-hexynyl and 5-hexynyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The term "aryl" means an unsaturated aromatic carbocyclic group which is moncyclic (eg phenyl) or polycyclic (eg naphthyl).

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

The term "ester" or "esterified carboxyl group" means a group $R_9$O(C=O)— in which $R_9$ is the group characterising the ester, notionally derived from the alcohol $R_9$OH.

The term "thioester" means a group $R_9$S(C=O)— or $R_9$S(C=S)— or $R_9$O(C=S)— in which $R_9$ is the group characterising the thioester, notionally derived from the alcohol $R_9$OH or the thioalcohol $R_9$SH.

Unless otherwise specified in the context in which it occurs, the term "substituted" as applied to any moiety herein means substituted with up to four substituents, each of which independently may be ($C_1$-$C_6$)alkyl, ($C_1$-$C_6$) alkoxy, hydroxy, mercapto, ($C_1$-$C_6$)alkylthio, amino, halo (including fluoro, chloro, bromo and iodo), nitro, trifluoromethyl, —COOH, —CONH$_2$, —CN, —COOR$^A$, —CONHR$^A$ or —CONHR$^A$R$^A$ wherein R$^A$ is a ($C_1$-$C_6$)alkyl group or the residue of a natural alpha-amino acid.

The term "side chain of a natural or non-natural alpha-amino acid" means the group $R^1$ in a natural or non-natural amino acid of formula $NH_2$—CH($R^1$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, a-aminoadipic acid, α-amino-n-butyric acid, 3,4-dihydroxyphenylalanine, homoserine, α-methylserine, omithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$-$C_6$ alkyl ester), amino groups may be converted to amides (for example as a NHCOC$_1$-$C_6$ alkyl amide) or carbamates (for example as an NHC(=O) OC$_1$-$C_6$ alkyl or NHC(=O)OCH$_2$Ph carbamate), hydroxyl groups may be converted to ethers (for example an OC$_1$C$_6$ alkyl or a O($C_1$-$C_6$ alkyl)phenyl ether) or esters (for example a OC(=O)$C_1$-$C_6$ alkyl ester) and thiol groups may be converted to thioethers (for example a tert-butyl or benzyl thioether) or thioesters (for example a SC(=O)$C_1$-$C_6$ alkyl thioester).

Examples of side chains of non-natural alpha amino acids include those referred to below in the discussion of suitable $R_3$ groups for use in compounds of the present invention.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. In the compounds of the invention, the C atom carrying the hydroxamic acid and $R_1$ groups is predominantly in the S configuration, the C atom carrying the $R_2$ group is predominantly in the R configuration, and the C atom carrying the $R_3$ and $R_4$ groups is in either the R or S configuration, with the predominantly S configuration presently preferred.

As previously stated, the compounds with which the present invention is concerned are principally distinguished from the compounds disclosed in the prior patent publications listed above by the ester or thioester group $R_4$. Accordingly the groups R, $R_1$, $R_1$, $R_2$, and $R_3$, may include those which have been disclosed in the corresponding positions of compounds disclosed in any of those prior art patent publications listed above. Without limiting the generality of the foregoing, examples of substituents R, $R_1$, $R_1$, $R_2$, and $R_3$ are given below:

The group $R_1$ $R_1$ may be, for example, hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or $C_1$-$C_4$ alkyl, eg methyl, ethyl n-propyl or n-butyl, substituted by a phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or cyclohexyl, cyclooctyl, cycloheptyl, cyclopentyl, cyclobutyl, cyclopropyl, tetrahydropyranyl or morpholinyl.

Presently preferred $R_1$ groups include n-propyl, allyl, methoxy and thienylsulfanyl-methyl.

The group $R_2$ $R_2$ may for example be $C_1$-$C_{12}$ alkyl, $C_3$-$C_6$ alkenyl or $C_3$-$C_6$ alkynyl;

phenyl($C_1$-$C_6$ alkyl)-, phenyl($C_3$-$C_6$ alkenyl)- or phenyl($C_3$-$C_6$ alkynyl)- optionally substituted in the phenyl ring;

heteroaryl($C_1$-$C_6$ alkyl)-, heteroaryl($C_3$-$C_6$ alkenyl- or heteroaryl($C_3$-$C_6$ alkynyl)- optionally substituted in the heteroaryl ring;

4-phenylphenyl($C_1$-$C_6$ alkyl)-, 4-phenylphenyl($C_3$-$C_6$ alkenyl)-, 4-phenylphenyl($C_3$-$C_6$ alkynyl)-, 4-heteroarylphenyl($C_1$-$C_6$ alkyl)-, 4-heteroarylphenyl($C_3$-$C_6$ alkenyl)-, 4-heteroarylphenyl($C_3$-$C_6$ alkynyl)-, optionally substituted in the terminal phenyl or heteroaryl ring;

phenoxy($C_1$-$C_6$ alkyl)- or heteroaryloxy($C_1$-$C_6$ alkyl)- optionally substituted in the phenyl or heteroaryl ring;

Specific examples of such groups include methyl, ethyl, n- and iso-propyl, n-, iso- and tert-butyl, n-pentyl, n-hexyl, n-heptyl, n-nonyl, n-decyl, prop-2-yn-1-yl, 3-phenylprop-2-yn-1-yl, 3-(2-chlorophenyl)prop-2-yn-1-yl, phenylpropy, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-phenyl)phenyl)prop-2-yn-1-yl and 3-[(4-chlorophenyl)phenyl]propyl-.

Presently preferred $R_2$ groups include isobutyl, n-hexyl, 3-(2-chlorophenyl)prop-2-yn-1-yl.

The group $R_3$ $R_3$ may for example be $C_1$-$C_6$ alkyl, phenyl, 2-, 3-, or 4-hydroxyphenyl, 2-, 3-, or 4-methoxyphenyl, 2-, 3-, or 4-pyridylmethyl, benzyl, 2-, 3-, or 4-hydroxybenzyl, 2-, 3-, or 4-benzyloxybenzyl, 2-, 3-, or 4-$C_1$-$C_6$ alkoxybenzyl, or benzyloxy($C_1$-$C_6$alkyl)- group; or the characterising group of a natural α amino acid, in which any functional group may be protected, any amino group may be acylated and any carboxyl group present may be amidated; or a group -[Alk]$_n$$R_6$ where Alk is a ($C_1$-$C_6$)alkyl or ($C_2$-$C_6$) alkenyl group optionally interrupted by one or more —O—, or —S— atoms or —N($R_7$)— groups [where $R_7$ is a hydrogen atom or a ($C_1$-$C_6$)alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$-$C_8$)alkoxy, phenyl($C_1$-$C_6$)alkoxy, ($C_1$-$C_6$)alkylamino, di(($C_1$-$C_6$)alkyl)amino, phenyl($C_1$-$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$) alkylamino, di-($C_1$-$C_6$)alkylamino, mercapto, ($C_1$-$C_6$) alkylthio, hydroxy($C_1$-$C_6$)alkyl, mercapto($C_1$-$C_6$)alkyl or ($C_1$-$C_6$)alkylphenylmethyl; or a group —CR$_a$R$_b$R$_c$ in which:

each of R$_a$, R$_b$ and R$_c$ is independently hydrogen, ($C_1$-$C_6$) alkyl, ($C_2$-$C_6$)alkenyl, ($C_2$-$C_6$)alkynyl, phenyl($C_1$-$C_6$) alkyl, ($C_3$-$C_8$)cycloalkyl; or R$_c$ is hydrogen and R$_a$ and R$_b$ are independently phenyl or heteroaryl such as pyridyl; or R$_c$ is hydrogen, ($C_1$-$C_6$)alkyl, ($C_2$-$C_6$)alkenyl, ($C_2$-$C_6$) alkynyl, phenyl($C_1$-$C_6$)alkyl, or ($C_3$-$C_6$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamatyl); or R$_a$ and R$_b$ are each independently ($C_1$-$C_6$)alkyl, ($C_2$-$C_6$) alkenyl, ($C_2$-$C_6$)alkynyl, phenyl($C_1$-$C_6$)alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, ($C_1$-$C_4$)perfluoroalkyl, —CH$_2$OH, —CO$_2$($C_1$-$C_6$)alkyl, —O($C_1$-$C_6$)alkyl, —O($C_2$-$C_6$)alkenyl, —S($C_1$-$C_6$)alkyl, —SO($C_1$-$C_6$)alkyl, —SO$_2$($C_1$-$C_6$) alkyl, —S($C_2$-$C_6$) alkenyl, —SO($C_2$-$C_6$)alkenyl, —SO$_2$($C_2$-$C_6$)alkenyl or a group —Q—W wherein Q represents a bond or —O—, S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$-$C_6$)alkyl, —CONH$_2$, —CONH($C_1$-$C_6$)alkyl, —CONH($C_1$-$C_6$alkyl)$_2$, —CHO, —CH$_2$OH, ($C_1$-$C_4$)perfluoroalkyl, —O($C_1$-$C_6$)alkyl, —S($C_1$-$C_6$) alkyl, —SO($C_1$-$C_6$)alkyl, —SO$_2$($C_1$-$C_6$)alkyl, —NO$_2$, —NH$_2$, —NH($C_1$-$C_6$)alkyl, —N(($C_1$-$C_6$)alkyl)$_2$, —NHCO($C_1$-$C_6$)alkyl, ($C_1$-$C_6$)alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl.

Examples of particular $R_3$ groups include benzyl, phenyl, cyclohexylmethyl, pyridin-3-ylmethyl, tert-butoxymethyl, iso-butyl, sec-butyl, tert-butyl, 1-benzylthio-1-methylethyl, 1-methylthio-1-methylethyl, and 1-mercapto-1-methylethyl.

Presently preferred $R_3$ groups include phenyl, benzyl, tert-butoxymethyl and iso-butyl.

The group $R_4$

Examples of particular ester and thioester groups $R_4$ groups include those of formula —(C=O)O$R_9$, —(C=O)S$R_9$, —(C=S)S$R_9$, and —(C=S)O$R_9$ wherein $R_9$ is ($C_1$-$C_6$)alkyl, ($C_2$-$C_6$)alkenyl, cycloalkyl, cycloalkyl($C_1$-$C_6$) alkyl-, phenyl, heterocyclyl, phenyl($C_1$-$C_6$)alkyl-, heterocyclyl($C_1$-$C_6$)alkyl-, ($C_1$-$C_6$)alkoxy($C_1$-$C_6$)alkyl-, ($C_1$-$C_6$)alkoxy($C_1$-$C_6$)alkoxy($C_1$-$C_6$)alkyl-, any of which may be substituted on a ring or non-ring carbon atom or on a ring heteroatom, if present. Examples of such $R_9$ groups include methyl, ethyl, n-and iso-propyl, n-, sec- and tert-butyl, 1-ethyl-prop-1-yl, 1-methyl-prop-1-yl, 1-methyl-but-1-yl, cyclopentyl, cyclohexyl, allyl, phenyl, benzyl, 2-, 3- and 4-pyridylmethyl, N-methylpiperidin-4-yl, 1-methylcyclopent-1yl, adamantyl, tetrahydrofuran-3-yl and methoxyethyl.

Presently preferred are compounds of formula (IB) wherein $R_4$ is a carboxylate ester of formula —(C=O)O$R_9$, wherein $R_9$ is benzyl, cyclopentyl, isopropyl or tert-butyl.

The group R

Presently preferred R groups are hydrogen and methyl.

Specific examples of compounds of the invention include those prepared according to Examples 1–3 and 5–43 below, and salts, hydrates and solvates thereof. Compounds presently preferred for their potencies as inhibitors of proliferation of various rapidly dividing tumour cells are:

2S-(3S-Hydroxycarbamoyl-2R-isobutyl-hex-5-enoylamino)-3-phenylpropionic acid cyclopentyl ester, 2S-(3S-Hydroxycarbamoyl-2R-isobutyl-hex-5-enoylamino)-3-phenylpropionic acid benzyl ester, 2S-{1R-[1S-Hydroxycarbamoyl-2-(thiophen-2-ylsulphanyl)-ethyl]-4-methyl-pentanoylamino}-3-phenyl-propionic acid isopropyl ester, 2S-(3S-Hydroxycarbamoyl-2R-isobutyl-hex-5-enoylamino)-4-methyl-pentanoic acid cyclopentyl ester, and pharmaceutically acceptable salts, hydrates and esters thereof.

Compounds according to the present invention wherein $R_4$ is a carboxylate ester group may be prepared by a process comprising causing an acid of general formula (II)

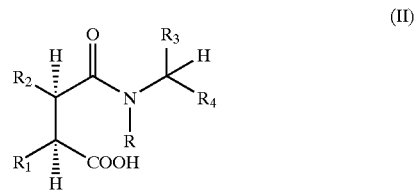

(II)

or an activated derivative thereof to react with hydroxylamine, O-protected hydroxylamine, or an N,O-diprotected hydroxylamine, or a salt thereof, R, $R_1$, $R_2$, $R_3$, and $R_4$ being as defined in general formula (I) except that any substituents in $R_1$, $R_2$, $R_3$, and $R_4$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, and $R_4$.

Conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

Compounds of formula (II) may be prepared by a process comprising: coupling an acid of formula (III) or an activated derivative thereof with an amine of formula (IV)

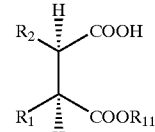

(III)

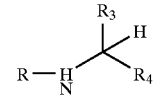

(IV)

wherein R, $R_1$, $R_2$, $R_3$, and $R_4$ are as defined in general formula (I) except that any substituents in $R_1$, $R_2$, $R_3$, and $R_4$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, and $R_4$.

Compounds of the invention wherein $R_4$ is a thioester may be prepared by coupling a compound of formula (IIIA) or an activated derivative thereof

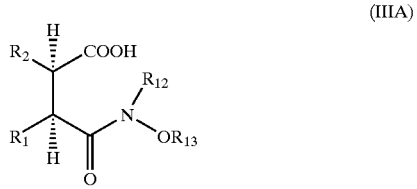

(IIIA)

wherein $R_1$ and $R_2$ are are as defined in general formula (I) and $R_{12}$ and $R_{13}$ are respectively N- and O-protecting groups, with a compound of formula (IV) above wherein $R_4$ is a thioester group, and selectively removing the O- and N-protecting groups from the hydroxamic acid group.

Active derivatives of acids (III) and (IIIA) include activated esters such as the pentafluorophenyl ester, acid anhydrides and acid halides, eg chlorides. Suitable hydroxy protecting groups may be selected from those known in the art.

Amino acid esters and thioesters of formula (IV) are either known or are prepared by routine known synthetic methods.

As mentioned above, compounds of formula (I) above, and those of formula (I) excluded by the provisos in the definition of formula (I) above, are useful in human or veterinary medicine since they are active as inhibitors of the proliferation of cancer cells. The utility of the invention therefore lies in the treatment of cancers, such as those caused by over-proliferation of lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma, glioblastoma or endothelioma cells. It will be understood that different compounds (I) will have differing potencies as proliferation inhibitors depending on the the type of cancer being treated. The activity of any particular compound (I) in inhibiting proliferation of any particular cell type may be routinely determined by standard methods, for example analogous to those described in the Biological Example herein. From the fact that compounds (I) which are poorly active as inhibitors of MMPs are nonetheless active in inhibiting proliferation of cancer cells, it is inferred that their utility in treating cancers is different from or supplementary to the utility of effective MMP inhibitors in the treatment of cancers.

In a further aspect of the invention there is provided a pharmaceutical or veterinary composition comprising a compound of the invention as defined by reference to formula (IB) above, together with a pharmaceutically or veterinarily acceptable excipient or carrier. One or more compounds of the invention may be present in the composition together with one or more excipient or carrier.

The compounds with which the invention is concerned may be prepared for administration by any route consistent with their pharmacokinetic properties.

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerin, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples 1–3 and 5–43 illustrate embodiments of the invention. Example 4 describes the preparation of a compound for comparison with those of the invention. The following abbreviations have been used in the examples DCM—Dichloromethane DMF—N,N-Dimethylformamide NMM—N-Methylmorpholine TFA—Trifluoroacetic acid HOBT—1-Hydroxybenzotriazole Column chromatography was performed with flash grade silica gel. $^1$H-NMR and $^{13}$C-NMR were recorded on a Bruker AC 250E spectrometer at 250.1 and 62.6 MHz respectively. CDCl$_3$ methanol-d$_4$ and dimethysulphoxide-d$_8$ (DMSO-d$_6$) were used as solvents and internal reference and spectra are reported as δ ppm from TMS.

EXAMPLE 1

2S-(3S-Hydroxycarbamoyl-2R-isobutyl-hex-5-enoylamino)-3-phenylpropionic acid methyl ester

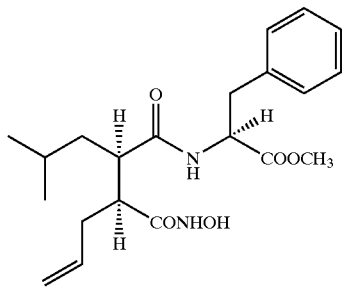

(a) 2S-(3S-tert-Butoxycarbonyl-2R-isobutyl-hex-5-enoylamino)-3-phenylpropionic acid methyl ester.

A solution of L-phenylalanine methyl ester hydrochloride (3.9 g, 17.9 mmol) and NMM (2.0 mL, 17.9 mmol) in DMF (15 mL) was cooled in an ice-water bath and treated with 3S-tert-butoxycarbonyl-2R-isobutyl-hex-5-enoic acid pentafluorophenyl ester (6.5 g, 14.9 mmol, WO 94/21625). The reaction was allowed to warm to room temperature and stirred overnight. The reaction mixture was concentrated under reduced pressure and the residue taken up in ethyl acetate and washed with 1 M hydrochloric acid, 1 M sodium carbonate and brine. The solution was dried over sodium sulphate, filtered and concentrated under reduced pressure to provide 2S-(3S-tert-butoxycarbonyl-2R-isobutyl-hex-5-enoylamino)-3-phenylpropionic acid methyl ester as a yellow solid (4.0 g, 52%). $^1$H-NMR; δ (CDCl$_3$), 7.28–7.07 (5H, m), 6.58 (1H, d), 5.75–4.94 (1H, m), 5.07–4.75 (3H, m), 3.53 (3H, s), 3.13 (1H, dd), 2.97 (1H, dd), 2.45–2.22 (3H, m), 1.96–1.01 (2H, m), 1.38 (9H, s), 0.98–0.72 (2H, m) and 0.78–0.72 (6H, m).

(b) 2S-(3S-Hydroxycarbonyl-2R-isobutyl-hex-5-enoylamino)-3-phenylpropionic acid methyl ester.

A solution of 2S-(3S-tert-butoxycarbonyl-2R-isobutyl-hex-5-enoylamino)-3-phenylpropionic acid methyl ester (4.0 g, 9.3 mmol) in a mixture of TFA and DCM (1:1, 10 mL) was allowed to stand at 5° C. overnight. The reaction mixture was concentrated under reduced pressure. Crystallisation of the product from ethyl acetate/hexane gave 2S-(3S-hydroxycarbonyl-2R-isobutyl-hex-5-enoylamino)-3-phenylpropionic acid methyl ester as a white solid (2.02 g, 58%). $^1$H-NMR; δ (CDCl$_3$), 7.28–7.08 (5H, m), 5.57–5.42 (1H, m), 4.85–4.74 (3H, m), 3.68 (3H, s), 3.25 (1H, dd), 2.88 (1H, dd), 2.55 (2.42 (1H, m), 2.38–2.24 (1H, m), 1.90–1.75 (1H, m), 1.62–1.40 (3H, m), 1.08–0.92 (1H, m), 0.88 (3H, d) and 0.79 (3H, d).

(c) 2S-(3S-Hydroxycarbamoyl-2R-isobutyl-hex-5-enoylamino)-3-phenylpropionic acid methyl ester.

A solution of 2S-(3S-hydroxycarbonyl-2R-isobutyl-hex-5-enoylamino)-3-phenylpropionic acid methyl ester (2.02 g, 5.38 mmol) in DMF (15 mL) was cooled in an ice-water bath. N-(3-dimethylaminopropyl)-N'-ethylcarbodiimide hydrochloride (1.24 g, 5.38 mmol) and HOBT (873 mg, 6.46 mmol) were added with stirring. The reaction was allowed to warm to room temperature and after 2 hours a solution of hydroxylamine hydrochloride (561 mg, 8.07 mmol) and NMM (0.9 mL, 8.07 mmol) in DMF (5 mL) added. After stirring overnight the reaction mixture was concentrated under reduced pressure. The residue was treated with a 2:1 mixture of ether/water to precipitate a white solid. The product was recrystallised from methanol to yield 2S-(3S-hydroxycarbamoyl-2R-isobutyl-hex-5-enoylamino)-3-phenylpropionic acid methyl ester as a white solid (309 mg, 15%). $^1$H-NMR; δ (methanol-d$_4$), 8.67 (1H, d, J=7.7 Hz), 7.23–7.14 (5H, m), 5.45–6.32 (1H, m), 4.85–4.74 (3H, m), 3.68 (3H, s), 3.24–3.09 (1H, m), 2.91–2.66 (1H, m), 2.47–2.39 (1H, m), 2.01–1.76 (2H, m), 1.49–1.36 (3H, m), 1.09–0.95 (1H, m), 0.85 (3H, d, J=6.4 Hz) and 0.80 (3H, d, J=6.4 Hz); $^{13}$C-NMR; δ (methanol-d$_4$), 176.5, 173.3, 172.4, 138.4, 136.1, 130.2, 129.5, 128.0, 117.3, 65.3, 55.1, 55.0, 52.7, 41.6, 38.1, 35.7, 26.7, 24.6 and 21.6.

EXAMPLE 2

2S-(3S-Hydroxycarbamoyl-2R-isobutyl-hex-5-enoylamino)-3-phenylpropionic acid ethyl ester

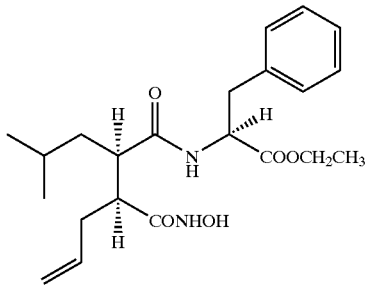

(a) 2S-(3S-tert-Butoxycarbonyl-2R-isobutyl-hex-5-enoylamino)-3-phenylpropionic acid ethyl ester.

A solution of L-phenylalanine ethyl ester (4.3 g, 22.0 mmol) in DMF (20 mL) was cooled in an ice-water bath and treated with 3S-tert-butoxycarbonyl-2R-isobutyl-hex-5-enoic acid pentafluorophenyl ester (10.7 g, 24.0 mmol). The reaction was stirred at 35° C. overnight. The reaction mixture was concentrated under reduced pressure and the residue taken up in ethyl acetate and washed with 1M hydrochloric acid, 1M sodium carbonate and brine. The solution was dried over sodium sulphate, filtered and concentrated under reduced pressure to provide 2S-(3S-tert-butoxycarbonyl-2R-isobutyl-hex-5-enoylamino)-3-phenylpropionic acid ethyl ester as a yellow solid (13.7 g, used directly in (b)). $^1$H-NMR; δ (CDCl$_3$), 7.35–7.12 (5H, m), 6.25 (1H, d), 5.84–5.50 (1H, m), 5.18–5.02 (1H, m), 4.99–4.89 (2H, m), 4.15–4.08 (2H, m), 3.20 (1H, dd), 3.06 (1H, dd), 2.52–2.32 (1H, m), 1.95–1.82 (2H, m), 1.72–1.55 (2H, m), 1.42 (9H, s), 1.28–1.21 (3H, m), 0.98–0.93 (2H, m) and 0.88–0.80 (6H, m).

(b) 2S-(3S-Hydroxycarbonyl-2R-isobutyl-hex-5-enoylamino)-3-phenylpropionic acid ethyl ester A solution of 2S-(3S-tert-butoxycarbonyl-2R-isobutyl-hex-5-enoylamino)-3-phenylpropionic acid ethyl ester (13.7 g, 31.0 mmol) in a mixture of TFA and DCM (1:1, 10 mL) was allowed to stand at room temperature overnight. The reaction mixture was concentrated under reduced pressure. Crystallisation of the product from ethyl acetate/hexane gave 2S-(3S-hydroxycarbonyl-2R-isobutyl-hex-5-enoylamino)-3-phenylpropionic acid ethyl ester as a white solid (1.5 g, 12%). $^1$H-NMR; δ (CDCl$_3$), 7.35–7.28 (3H, m), 7.18–7.10 (2H, m), 6.22 (1H, d), 5.77–5.60 (1H, m), 5.08–4.99 (3H, m), 4.22 (2H, q), 3.24 (1H, dd), 3.07 (1H, dd), 2.61–2.52 (1H, m), 2.45–2.28 (2H, m), 2.08–1.94 (1H, m), 1.75–1.64 (1H, m), 1.60–1.45 (1H, m), 1.28 (3H, t), 1.21–1.09 (1H, m) and 0.86 (6H, d).

(c) 2S-(3S-Hydroxycarbamoyl-2R-isobutyl-hex-5-enoylamino)-3-phenylpropionic acid ethyl ester.

A solution of 2S-(3S-hydroxycarbonyl-2R-isobutyl-hex-5-enoylamino)-3-phenylpropionic acid ethyl ester (2.2 g, 5.38 mmol) in DMF (20 mL) was cooled in an ice-water bath. N-(3-dimethylamino propyl)-N'-ethylcarbodiimide hydrochloride (1.3 g, 6.78 mmol) and HOBT (916 mg, 6.78 mmol) were added with stirring. The reaction was allowed to warm to room temperature and after 2 hours a solution of hydroxylamine hydrochloride (589 mg, 8.48 mmol) and NMM (0.9 mL, 8.48 mmol) in DMF (10 mL) added. After stirring overnight the reaction mixture was concentrated under reduced pressure. The residue was treated with a 2:1 mixture of ether/water to precipitate a white solid which was collected by filtration and washed with hot ethyl acetate. Drying under vacuum provided 2S-(3S-hydroxycarbamoyl-2R-isobutyl-hex-5-enoylamino)-3-phenylpropionic acid ethyl ester as a white solid (1.8 g, 79%). $^1$H-NMR; δ (methanol-d$_4$), 8.65 (1H, d, J=8.4 Hz), 7.81–7.09 (5H, m), 5.45–5.32 (1H, m), 4.89–4.71 (3H, m), 4.13 (2H, q, J=7.1 Hz), 3.23–3.06 (2H, m), 2.48–2.38 (1H, m), 2.02–1.75 (3H, m), 1.51–1.30 (2H, m), 1.21 (3H, t, J=7.1 Hz), 1.01–0.90 (1H, m), 0.86 (3H, d, J=6.4 Hz) and 0.79 (3H, d, J=6.4 Hz); $^{13}$C-NMR; δ (methanol-d$_4$), 176.5, 172.9, 172.4, 138.4, 136.1, 130.3, 129.5, 128.0, 117.3, 65.1, 62.4, 56.5, 55.2, 55.1, 54.6, 43.4, 41.6, 38.2, 37.3, 35.7, 27.0, 26.6, 24.6, 21.7, 15.7 and 14.5.

EXAMPLE 3

2S-(3S-Hydroxycarbamoyl-2R-isobutyl-hex-5-enoylamino)-3-phenylpropionic acid isopropyl ester

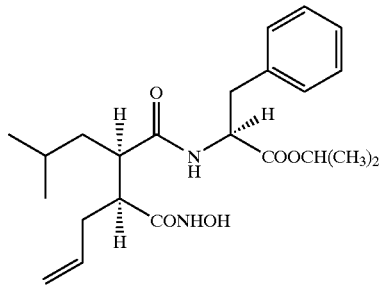

(a) 2S-(3S-tert-Butoxycarbonyl-2R-isobutyl-hex-5-enoylamino)-3-phenylpropionic acid isopropyl ester.

A solution of L-phenylalanine isopropyl ester (3.9 g, 18.8 mmol) in DMF (15 mL) was cooled in an ice-water bath and treated with 3S-tert-butoxycarbonyl-2R-isobutyl-hex-5-enoic acid pentafluorophenyl ester (9.03 g, 20.7 mmol). The reaction was allowed to warm to room temperature and stirred overnight. The reaction mixture was concentrated under reduced pressure. The residue was taken up in ethyl acetate and washed with 1M hydrochloric acid, 1M sodium carbonate and brine. The solution was dried over sodium sulphate, filtered and concentrated under reduced pressure. The product was purified by column chromatography using a gradient elution of 100% DCM to 10% methanol/DCM. Product containing fractions were combined and solvent removed to yield 2S-(3S-tert-butoxycarbonyl-2R-isobutyl-hex-5-enoylamino)-3-phenylpropionic acid isopropyl ester as a yellow solid (3.5 g, 41%). $^1$H-NMR; δ (CDCl$_3$), 7.44–7.15 (5H, m), 6.46 (1H, d), 5.72–5.48 (1H, m), 5.15–4.88 (3H, m), 3.25 (1H, dd), 3.11 (1H, dd), 2.60–2.48 (2H, m), 2.00–1.78 (1H, m), 1.72–1.58 (1H, m), 1.45 (9H, s), 1.35–1.18 (9H, m), 0.98–0.91 (1H, m) and 0.88–0.80 (6H, m).

(b) 2S-(3S-Hydroxycarbonyl-2R-isobutyl-hex-5-enoylamino)-3-phenylpropionic acid isopropyl ester A solution of 2S-(3S-tert-butoxycarbonyl-2R-isobutyl-hex-5-enoylamino)-3-phenylpropionic acid isopropyl ester (3.5 g, 7.6 mmol) in a mixture of TFA and DCM (1:1, 10 mL) was allowed to stand at 5° C. overnight. The reaction mixture was concentrated under reduced pressure. Addition of ether to the residue gave 2S-(3S-hydroxycarbonyl-2R-isobutyl-hex-5-enoylamino)-3-phenylpropionic acid isopropyl ester as a white solid (261 mg, 8%). $^1$H-NMR; δ (CDCl$_3$), 7.38–7.25 (3H, m), 7.18–7.12 (2H, m), 6.49 (1H, d), 5.70–5.55 (1H, m), 5.13–4.89 (3H, m), 3.24 (1H, dd), 3.05 (1H, dd), 2.63–2.45 (2H, m), 2.28–2.15 (1H, m), 2.02–1.79 (1H, m), 1.70–1.61 (1H, m), 1.58–1.40 (1H, m), 1.32–1.18 (7H, m), 0.98–0.91 (1H, m), 0.85–0.82 (6H, m).

(c) 2S-(3S-Hydroxycarbamoyl-2R-isobutyl-hex-5-enoylamino)-3-phenylpropionic acid isopropyl ester.

A solution of 2S-(3S-hydroxycarbonyl-2R-isobutyl-hex-5-enoylamino)-3-phenylpropionic acid isopropyl ester (260 mg, 0.64 mmol) in DMF (10 mL) was cooled in an ice-water bath. N-(3-dimethylaminopropyl)-N'-ethylcarbodiimide hydrochloride (148 mg, 0.77 mmol) and HOBT (104 mg, 0.77 mmol) were added with stirring. The reaction was allowed to warm to room temperature and after 2 hours a solution of hydroxylamine hydrochloride (67 mg, 0.96 mmol) and NMM (0.1 mL, 0.96 mmol) in DMF (5 mL) added. After stirring overnight the reaction mixture was concentrated under reduced pressure and the product was purified by chromatography on acid-washed silica using 5–10% methanol in DCM. Recrystallisation from from ethy acetate/hexane provided 2S-(3S-hydroxycarbamoyl-2R-isobutyl-hex-5-enoylamino)-3-phenylpropionic acid isopropyl ester as a white solid (12 mg, 4%). $^1$H-NMR; δ (methanol-d$_4$), 8.64 (1H, d, J=8.2 Hz), 7.23–7.11 (5H, m), 5.41–5.34 (1H, m), 5.02–4.92 (1H, m), 4.85–4.69 (2H, m), 3.23–3.16 (1H, m), 2.89–2.80 (1H, m), 2.46–2.39 (1H, m), 2.01–1.79 (2H, m), 1.50–1.42 (2H, m), 1.23–1.56 (7H, m), 0.99–0.95 (1H, m), 0.86 (3H, d, J=6.3 Hz), and 0.80 (3H, d, J=6.4 Hz); $^{13}$C-NMR; δ (methanol-d$_4$), 176.4, 176.3, 138.4, 136.1, 130.3, 129.5, 123.0, 117.3, 70.2, 55.4, 41.6, 38.3, 35.7, 26.6, 24.5, 22.0, 21.9 and 21.7.

EXAMPLE 4

(For comparison)

3S-(2-Phenyl-1R-methylcarboxy-ethylcarbamoyl)-2R, 5-dimethylhexanohydroxamic acid

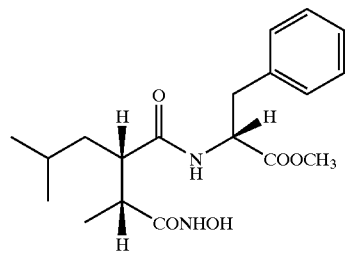

(a) 3S-(2-Phenyl-1R-methylcarboxy-ethylcarbamoyl)-2-benzyloxycarbonyl-5-methylhexanoic acid benzyl ester A solution of 3S-hydroxycarbonyl-2-benzyloxycarbonyl-5-methylhexanoic acid benzyl ester (10.0 g, 25 mmol, WO 90/05719) in DMF (100 mL) was treated with HOBT (5.1 g, 38 mmol), N-(3-dimethylaminopropyl)-N'-ethylcarbodiimide hydrochloride (5.9 g, 30 mmol), D-phenylalanine methyl ester (5.2 g, 29 mmol) and NMM (4.1 mL, 38 mmol). The yellow reaction mixture was stirred at room temperature overnight and concentrated under reduced pressure. The residue was taken up in ethyl acetate and washed with 1M hydrochloric acid (x2), saturated sodium bicarbonate (x2) and brine. The solution was dried over magnesium sulphate, filtered and concentrated to provide 3S-(2-phenyl-1R-methylcarboxy-ethylcarbamoyl)-2-benzyloxycarbonyl-5-methylhexanoic acid benzyl ester as colourless oil (12.2 g, 87%). $^1$NMR; δ (CDCl$_3$), 7.41–7.17 (15H, m), 6.25 (1H, d, J=7.9 Hz), 5.22–5.04 (4H, m), 4.90–4.83 (1H, m), 3.86 (1H, d, J=10.1 Hz), 3.67 (3H, s), 3.11 (1H, dd, J=13.8, 5.6 Hz), 3.02–2.91 (2H, m), 1.69–1.54 (1H, m), 1.53–1.46 (1H, m), 1.05–0.96 (1H, m), 0.79 (3H, d, J=6.5 Hz) and 0.78 (3H, d, J=6.4 Hz).

(b) 3S-(2-Phenyl-1R-methylcarboxy-ethylcarbamoyl)-2-methylene-5-methylhexanoic acid A solution of 3S-(2-phenyl-1R-methylcarboxy-ethylcarbamoyl)-2-benzyloxycarbonyl-5-methylhexanoic acid benzyl ester (3.4 g, 6.1 mmol) in ethanol (30 mL), was treated under an inert atmosphere with palladium catalyst (100 mg, 10% on charcoal) and then stirred under an atmosphere of hydrogen gas for 1 hour. The catalyst was removed by filtration through a glass fibre pad. The filtrate was treated with piperidine (0.7 mL) and formaldehyde (3.2 mL of a 37% wt aqeous solution, 7.05 mmol) and allowed to stand at room temperature overnight. The reaction mixture was concentrated under reduced pressure and the residue partitioned between ethyl acetate and saturated sodium bicarbonate solution. The aqueous layer was separated, acidified with 1M hydrochloric acid to pH 1 and extracted with ethyl acetate. The organic extracts were dried over magnesium sulphate. filtered and concentrated under reduced pressure to yield 3S-(2-phenyl-1R-methylcarboxyethylcarbamoyl)-2-methylene-5-methylhexanoic acid as a white solid (1.05 g, 50%). $^1$NMR; δ (CDCl$_3$), 7.26–7.14 (3H, m), 7.06–7.02 (2H, m), 6.57 (1H, d, J=8.0), 6.44 (1H, s), 5.88 (1H, s), 4.93–4.81 (1H, m), 3.72 (3H, s), 3.54–3.48 (1H, m), 3.13 (1H, dd, J=13.9, 5.7 Hz), 3.02 (1H, dd, J=13.8, 6.4 Hz), 1.85–1.76 (1H, m), 1.58–1.41 (2H, m) and 0.90–0.85 (6H, m).

(c) 3S-(2-Phenyl-1R-methylcarboxy-ethylcarbamoyl)-2R,5-dimethylhexanoic acid

A solution of 3S-(2-phenyl-1R-methylcarboxy-ethylcarbamoyl)-2-methylene-5-methylhexanoic acid (960 mg, 2.77 mmol) in ethanol was treated under an inert atmosphere with palladium catalyst (50 mg, 10% on charcoal). The reaction mixture was stirred under an atmosphere of hydrogen gas for 90 minutes. The catalyst was removed by filtration through a glass fibre pad. The filtrate was concentrated under reduced pressure to yield 3S-(2-phenyl-1R-methylcarboxy-ethylcarbamoyl)-2R,5-dimethylhexanoic acid as a white solid (900 mg, 93%). $^1$NMR; δ (CDCl$_3$), 7.33–7.20 (3H, m), 7.15–7.11 (2H, m), 6.25 (1H, d, J=8.1 Hz), 4.99–4.90 (1H, m), 3.75 (3H, s), 3.19 (1H, dd, J=13.9, 5.5 Hz), 3.05 (1H, dd, J=14.0, 7.3 Hz), 2.63–2.54 (1H, m), 2.47–2.41 (1H, m), 1.73–1.61 (1H, m), 1.60–1.44 (1H, m), 1.20–1.10 (1H, m), 1.03 (3H, d, J=7.1 Hz), 0.86 (3H, d, J=6.5 Hz) and 0.85 (3H, d, J=6.5 Hz).

(d) 3S-(2-Phenyl-1R-methylcarboxy-ethylcarbamoyl)-2R,5-dimethylhexanohydroxamic acid A solution of 3S-(2-phenyl-1R-methylcarboxy-ethylcarbamoyl)-2R,5-dimethylhexanoic acid (850 mg, 2.44 mmol), HOBT (395 mg, 2.92 mmol), O-benzylhydroxylamine (360 mg, 2.92 mmol) and N-(3-dimethylaminopropyl)-N'-ethylcarbodiimide hydrochloride (560 mg, 2.92 mmol) was stirred at room temperature for 96 hours. The reaction mixture was concentrated under reduced pressure to a colourless oil. The residue was taken up in ethyl acetate and washed with 2M hydrochloric acid (x2), saturated sodium bicarbonate (x2) and brine. The solution was dried over magnesium sulphate, filtered and concentrated under reduced pressure to a white solid. The solid was taken up in a 10% mixture of cyclohexane and ethanol (40 mL), treated with palladium catalyst (50 mg, 10% on charcoal) and heated at 80° C. for 1 hour. The catalyst was removed by filtration and the filtrate concentrated under reduced pressure. The product was taken up in methanol and ether added to provide 3S-(2-phenyl-1R-methylcarboxy-ethylcarbamoyl)-2R,5-dimethylhexanohydroxamic acid as a white solid (340 mg, 38%). $^1$H-NMR; δ (methanol-d$_4$), 8.57 (1H, d, J=8.3 Hz), 7.23–7.04 (5H, m), 4.71–4.64 (1H, m), 3.60 (3H, s), 3.14 (1H, dd, J=14.0, 4.8 Hz), 2.81 (1H, dd, J=14.0, 10.7 Hz), 2.35 (1H, dt, J=10.9, 3.0 Hz), 2.01–1.91 (1H, m), 1.43–1.29 (2H, m), 0.92–0.82 (1H, m), 0.78 (3H, d, J=6.4 Hz), 0.72 (3H, d, J=6.5 Hz), and 0.49 (3H, d, J=6.8 Hz); $^{13}$C-NMR; δ (methanol-d$_4$), 178.0, 174.7, 161.0, 131.6, 129.1, 54.0, 50.0, 43.3, 43.0, 39.5, 26.1, 25.8, 23.0, 18.2 and 17.6.

EXAMPLE 5

3R-(2-Phenyl-1S-methylcarboxy-ethylcarbamoyl)-2S,5-dimethylhexanohydroxamic acid

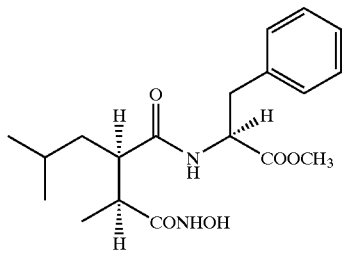

Using procedures similar to those described for example 4 and starting with 3R-hydroxycarbonyl-2-benzyloxycarbonyl-5-methylhexanoic acid benzyl ester (WO 90/05719) and L-phenylalanine methyl ester 3R-(2-phenyl-1S-methylcarboxy-ethylcarbamoyl)-2S,5-dimethylhexanohydroxamic acid was prepared as a white solid. $^1$H-NMR and $^{13}$C-NMR spectral data were directly analogous to those described for the enantiomer, example 4.

EXAMPLE 6

2S-(3S-Hydroxycarbamoyl-2R-isobutyl-hex-5-enoylamino)-3-phenyl-propionic acid tert-butyl ester

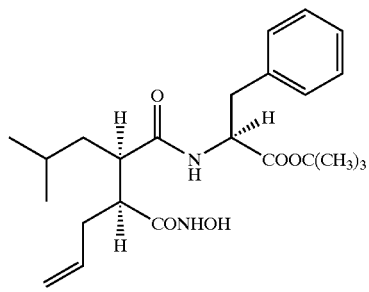

(a) 2S-[1R-(1S-tert-Butoxycarbonyl-2-phenyl-ethylcarbamoyl)-3-methyl-butyl]-pent-4-enoic acid allyl ester A solution of 2S-allyl-3R-isobutyl-succinic acid 1-allyl ester (830 mg, 3.3 mmol, WO97/18183), HOBt (504 mg, 3.7 mmol) and N-(3-dimethylaminopropyl)-N'-ethylcarbodiimide hydrochloride (714 mg, 3.7 mmol) in DMF (10 mL) was stirred for 10 minutes. A suspension of L-phenylalanine tert butyl ester hydrochloride (800 mg, 3.1 mmol) and NMM (376 µL, 3.4 mmol) in DMF (5 mL) was added dropwise to the reaction mixture. The reaction mixture was stirred for 18 hours at room temperature. The reaction mixture was concentrated under reduced pressure. The residue was taken up in ethyl acetate and washed with 1M hydrochloric acid, saturated sodium bicarbonate and brine. The organic solution was dried over magnesium sulphate, filtered and concentrated under reduced pressure. The product was purified by column chromatography on silica gel eluting with a gradient of 9:1 to 2:1 hexane/ethyl acetate. Product containing fractions was combined and solvent removed under reduced pressure to leave 2S-[1R-(1S-tert-butoxycarbonyl-2-phenyl-ethylcarbamoyl)-3-methyl-butyl]-pent-4-enoic acid allyl ester as a white solid (1.29 g, 91%). $^1$H-NMR; δ (CDCl$_3$), 7.32–7.16 (5H, m), 5.99 (1H, d, J=8.1 Hz), 5.89 (1H, ddt, J=17.2, 10.4, 5.8 Hz), 5.69–5.53 (1H, m), 5.32 (1H, dq, J=17.2, 1.5 Hz), 5.23 (1H, ddd, J=10.4, 1.3, 1.2 Hz), 4.96–4.77 (3H, m), 4.56 (2H, dd, J=5.8, 1.1 Hz), 3.15–2.96 (2H, m), 2.66 (1H, dt, J=9.7, 5.1 Hz), 2.38 (1H, dt, J=10.4, 3.3 Hz), 2.11–1.90 (2H, m), 1.71–1.59 (1H, m), 1.53–1.41 (1H, m), 1.40 (9H, s), 1.07–0.94 (1H, m), 0.85 (3H, d, J=6.5 Hz) and 0.83 (3H, d, J=6.5 Hz).

(b) 2S-[1R-(1S-tert-Butoxycarbonyl-2-phenyl-ethylcarbamoyl)-3-methyl-butyl]-pent-4-enoic acid A solution of 2S-[1R-(1S-tert-butoxycarbonyl-2-phenyl-ethylcarbamoyl)-3-methyl-butyl]-pent-4-enoic acid allyl ester (1.29 g, 2.82 mmol) in THF (15 mL) was treated with morpholine (300 µL) and tetrakis (triphenylphosphine) palladium (0) (40 mg) the reaction was allowed to stir at room temperature overnight. The reaction mixture was partitioned between ethyl acetate and 1M hydrochloric acid. The organic layer was dried over magnesium sulphate, filtered and concentrated under reduced pressure. The crude product was purified by column chromatography on silica gel eluting with 5% methanol in DCM. Product containing fractions were combined and solvent removed under reduced pressure to yield 2S-[1R-(1S-tert-butoxycarbonyl-2-phenyl-ethylcarbamoyl)-3-methyl-butyl]-pent-4-enoic acid as a white solid (423 mg, 34%). $^1$H-NMR; δ (CDCl$_3$), 7.34–7.20 (3H, m), 7.19–7.12 (2H, m), 6.20 (1H, d, J=7.9 Hz), 5.75–5.57 (1H, m), 4.79 (1H, dd, J=14.3, 6.5 Hz), 3.18 (1H, dd, J=14.0, 6.1 Hz), 3.03 (1H, dd, J=14.0, 6.8 Hz), 2.57–2.33 (3H, m), 2.08–1.94 (1H, m), 1.72–1.37 (2H, m), 1.44 (9H, s), 1.16 (1H, ddd, J=13.8, 9.8, 3.5 Hz) and 0.87–0.84 (6H, m).

(c) 2S-(3S-Hydroxycarbamoyl-2R-isobutyl-hex-5-enoylamino)-3-phenyl-propionic acid tert-butyl ester A solution of 2S-[1R-(1S-tert-butoxycarbonyl-2-phenyl-ethylcarbamoyl)-3-methyl-butyl]-pent-4-enoic acid (400 mg, 1.0 mmol), N-(3-dimethylaminopropyl)-N'-ethylcarbodiimide hydrochloride (232 mg, 1.2 mmol) and HOBT (164 mg, 1.2 mmol) in DMF (10 mL) was stirred at 0° C. for 2 hours. Hydroxylamine hydrochloride (105 mg, 1.5 mmol) was taken up in DMF (2 mL) and NMM (166 µL, 1.5 mmol) added. After 10 minutes the hydroxylamine solution was added to the reaction mixture which was allowed to stir at room temperature for 18 hours. DFM was removed under reduced pressure and the residue partitioned between ethyl acetate and 1.0M hydrochloric acid. The organic layer was separated and washed with saturated sodium bicarbonate and brine before drying over magnesium sulphate. Filtration, evaporation and recrystallization from hot ethyl acetate yielded 2S-(3S-hydroxycarbamoyl-2R-isobutyl-hex-5-enoylamino)-3-phenyl-propionic acid tert-butyl ester as a white solid (248 mg, 64%). $^1$H-NMR; δ (methanol-d$_4$), 8.52 (1H, d, J=8.4 Hz), 7.18–7.03 (5H, m), 5.34–5.28 (1H, m), 4.79–4.64 (2H, m), 4.62–4.55 (1H, m), 3.03 (1H, dd, J=13.9, 5.2 Hz), 2.77 (1H, dd, J=13.9, 10.5 Hz), 2.39–2.31 (1H, m), 1.96–1.85 (1H, m), 1.81–1.68 (1H, m), 1.44–1.22 (3H, m), 1.34 (9H, s), 0.94–0.89 (1H, m), 0.80 (3H, d, J=6.4 Hz) and 0.73 (3H, d, J=6.5 Hz). $^{13}$C-NMR; δ (methanol-d$_4$), 176.2, 172.4, 172.1, 138.4, 136.1, 130.3, 129.5, 127.9, 117.3, 82.8, 78.9, 55.8, 47.9, 41.6, 38.4, 35.7, 28.2, 26.6, 24.5 and 21.8.

EXAMPLE 7

2S-(2R-Hydroxycarbamoylmethyl-4-methyl-pentanoylamino)-3-phenyl-propionic acid isopropyl ester

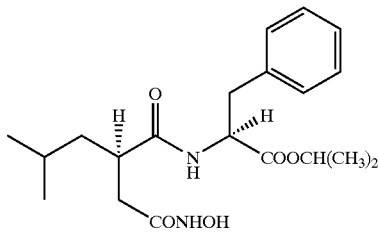

(a) 3R-(1S-Isopropoxycarbonyl-2-phenyl-ethylcarbamoyl)-5-methyl-hexanoic acid tert-butyl ester A solution of 3R-isobutyl-succinic acid 1-tert butyl ester (1.17 g, 5.1 mmol), L-phenylalanine isopropyl ester (1.17 g, 5.1 mmol), N-(3-dimethylaminopropyl)-N'-ethylcarbodiimide hydrochloride (972 mg, 5.1 mmol), and HOBT (685 mg, 5.1 mmol) in ethyl acetate (30 mL) was heated under reflux for 18 hours. The reaction mixture was diluted with ethyl acetate and washed with 1M hydrochloric acid, saturated sodium bicarbonate and brine before drying over magnesium sulphate, filtration and concentration under reduced pressure to yield 3R-(1S-isopropoxycarbonyl-2-phenyl-ethylcarbamoyl)-5-methyl-hexanoic acid tert-butyl ester as a white solid (1.95 g, ~100%). $^1$H-NMR; δ (CDCl$_3$), 7.29–7.17 (5H, m), 6.23 (1H, d, J=7.8 Hz), 5.00–4.93 (1H, m), 4.80–4.78 (1H, m), 3.08–3.05 (2H, m), 2.60–2.49 (1H, m), 2.30–2.24 (1H, m), A solution of 3R-(1S-isopropoxycarbonyl-2-phenyl-ethylcarbamoyl)-5-methyl-hexanoic acid tert-butyl ester (1.95 g, 4.9 mmol) in a 1:1 mixture of TFA:DCM (15 mL) was allowed to stand for 18 hours at room temperature. Solvent and excess TFA were removed under reduced pressure and the residue taken up in toluene and re-evaporated. 3R-(1S-Isopropoxycarbonyl-2-phenyl-ethylcarbamoyl)-5-methyl-hexanoic acid was produced as a colourless oil (1.9 g, contaminated with toluene). $^1$H-NMR; δ (CDCl$_3$) 7.32–7.14 (5H, m), 6.61 (1H, bs) 5.07–4.96 (1H, m), 4.91–4.83 (1H, m), 3.10 (2H, d, J=6.1 Hz), 2.74–2.66 (1H, m), 2.55–2.42 (1H, m), 1.68–1.49 (3H, m), 1.24–1.18 (6H, m) and 0.88 (6H, 2×d).

(c) 2S-(2R-Hydroxycarbamoylmethyl-4-methyl-pentanoylamino)-3-phenyl-propionic acid isopropyl ester.

A solution of 3R-(1S-isopropoxycarbonyl-2-phenyl-ethylcarbamoyl)-5-methyl-hexanoic acid (1.9 g, 5.23 mmol) was dissolved in DMF (15 mL), cooled in an ice-water bath and treated with HOBT (848 mg, 6.3 mmol) and N-(3-dimethylaminopropyl)-N'-ethylcarbodiimide hydrochloride (1.2 g, 6.3 mmol). After 1 hour a mixture of hydroxylamine hydrochloride (546 mg, 7.9 mmol) and NMM (794 mg, 7.9 mmol) in DMF (10 mL) was added. The reaction was stirred at room temperature for 96 hours. DMF was removed under reduced pressure and the residue partitioned between ethyl acetate and 2M hydrochloric acid. The organic layer was washed with distilled water, 5% aqueous sodium carbonate and water before drying over magnesium sulphate. The solution was filtered and concentrated under reduced pressure. Recrystallization from diethylether/hexane provided 2S-(2R-hydroxycarbamoylmethyl-4-methyl-pentanoylamino)-3-phenyl-propionic acid isopropyl ester as a white crystalline solid (270 mg, 14%). $^1$H-NMR; δ (methanol-d$_4$), 7.17–7.10 (5H, m), 4.90–4.79 (1H, m), 4.55–4.49 (1H, m), 3.18–2.97 (1H, dd), 2.92–2.85 (1H, dd), 2.78–2.62 (1H, m), 2.02–1.93 (2H, m), 1.48–1.36 (2H, m), 1.11 (3H, d, J=6.3 Hz), 1.02 (3H, d, J=6.3 Hz), 1.00 (1H, m), 0.80 (3H, d, J=6.4 Hz) and 0.76 (3H, d, J=6.4 Hz). $^{13}$C-NMR; δ (methanol-d$_4$) 178.4, 171.0, 139.6, 131.7, 130.8, 129.1, 71.4, 56.6, 43.3, 43.2, 41.2, 39.6, 38.3, 33.5, 28.2, 25.1, 23.6, 23.3 and 23.2.

EXAMPLE 8

2S-[2R-(S-Hydroxy-hydroxycarbamoyl-methyl)-4-methyl-pentanoylamine]-3-phenyl-propionic acid isopropyl ester

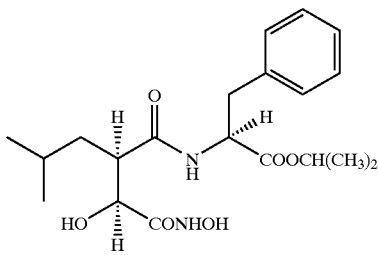

(a) 2S-[2R-(2,2-Dimethyl-5-oxo-[1,3]-dioxolan-4S-yl)-4-methyl-pentanoylamino]-3-phenylpropionic acid isopropyl ester.

A solution of 2R-(2,2-dimethyl-5-oxo-[1,3-dioxolan-4S-yl)-4-methyl-pentanoic acid pentafluorophenyl ester (WO 95/19956) (2.87 g, 7.3 mmol) and L-phenylalanine isopropyl ester (1.5 g, 7.3 mmol) in DCM was allowed to stand at room temperature for 96 hours. The reaction mixture was diluted with DCM and washed with 1M aqueous sodium carbonate, 1M hydrochloric acid and brine before drying over magnesium sulphate, filtration and concentration under reduced pressure. The product was recrystallised from ethyl acetate/hexane to yield 2S-[2R-(2,2-dimethyl-5-oxo-[1,3]-dioxolan-4S-yl)-4-methyl-pentanoylamino]-3-phenylpropionic acid isopropyl ester as fine white needles (810 mg, 29%). $^1$H-NMR; δ (CDCl$_3$), 7.35–7.17 (5H, m), 6.38 (1H, d, J=7.5 Hz), 5.06–4.99 (1H, m), 4.88–4.81 (1H, m), 4.50 (1H, d, J=5.9 Hz), 3.13–3.10 (2H, m), 2.73–2.65 (1H, m), 1.71–1.45 (3H, m), 1.57 (3H, s), 1.54 (3H, s), 1.22 (3H, d, J=6.2 Hz), 1.20 (3H, d, J=6.3 Hz), 0.90 (3H, d, J=6.1 Hz) and 0.88 (3H, d, J=6.2 Hz).

(b) 2S-[2R-(S-Hydroxy-hydroxycarbamoyl-methyl)-4-methyl-pentanoylamine]-3-phenyl-propionic acid isopropyl ester.

A solution of sodium methoxide (325 mg, 6.1 mmol) and hydroxylamine hydrochloride (396 mg, 6.1 mmol) in methanol (15 mL) was stirred at room temperature for 2 hours. The solution was then filtered into a solution of 2S-[2R-(2,2-dimethyl-5-oxo-[1,3]-dioxolan-4S-yl)-4-methyl-pentanoylamino]-3-phenylpropionic acid isopropyl ester (800 mg, 2.1 mmol) in methanol (10 mL). The reaction was allowed to stand at room temperature for 18 hours. The reaction mixture was concentrated under reduced pressure and the residue partitioned between ethyl acetate and water. The organic layer was washed with water, dried over magnesium sulphate, filtered and concentrated under reduced pressure. Recrystallisation from ethyl acetate gave 2S-[2R-(S-hydroxy-hydroxycarbamoyl-methyl)-4-methyl-pentanoylamine]-3-phenyl-propionic acid isopropyl ester as white crystalline material which was dried under vacuum (465 mg, 58%). $^1$H-NMR; δ (methanol-d$_4$), 7.17–7.12 (5H, m), 4.83–4.76 (1H, m), 4.53 (1H, t, J=7.2 Hz), 3.88 (1H, d, J=7.1 Hz), 2.95 (2H, d, J=7.1 Hz), 2.78–2.64 (1H, m), 1.55–1.29 (2H, m), 1.09 (3H, d, J=6.3 Hz), 1.08 (1H, m), 0;94 (3H, d, J=6.2 Hz), 0.81 (3H, d, J=6.5 Hz) and 0.76 (3H, d, J=6.5 Hz). $^{13}$C-NMR; δ (methanol-d$_4$), 175.7, 172.5, 171.5, 156.8, 138.0, 130.4, 129.4, 127.8, 73.2, 70.2, 55.4, 49.3, 39.2, 38.6, 26.6, 23.9, 22.1, 21.9 and 21.6.

EXAMPLE 9

2S-[2R-(1S-Hydroxycarbamoyl-ethyl)-4-methyl-pentanoylamino]-3-phenyl-propionic acid isopropyl ester

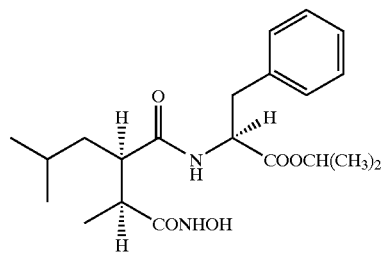

The title compound was prepared using procedures analogous to those described for example 4, starting with 2-benzyloxycarbonyl-3R-isobutyl-succinic acid 1-benzyl ester and L-phenylalanine isopropyl ester. $^1$H-NMR; δ (methanol-d$_4$), 7.18–7.05 (5H, m), 4.94–4.84 (1H, m), 4.65 (1H, dd, J=10.41, 5.0 Hz), 3.11 (1H, dd, J=14.0, 5.2 Hz), 2.79 (1H, dd, J=13.9, 10.5 Hz), 2.35 (1H, dt, J=11.0, 3.1 Hz), 1.98–1.91 (1H, m), 1.45–1.35 (2H, m), 1.14 (3H, d, J=6.3 Hz), 1.08 (3H, d, J=6.2 Hz), 0.92–0.81 (1H, m), 0.79 (3H, d, J=6.4 Hz), 0.72 (3H, d, J=6.5 Hz) and 0.47 (3H, d, J=6.8 Hz). $^{13}$C-NMR; δ (methanol-d$_4$), 176.5, 160.8, 159.2, 138.4, 130.3, 129.5, 127.8, 70.2, 55.3, 53.5, 49.3, 41.9, 41.7, 36.3, 26.7, 24.5, 22.0, 21.7, 21.7 and 16.5.

EXAMPLE 10

2S-(2R-Hydroxycarbamoylmethyl-octanoylamino)-3-phenyl-propionic acid isopropyl ester

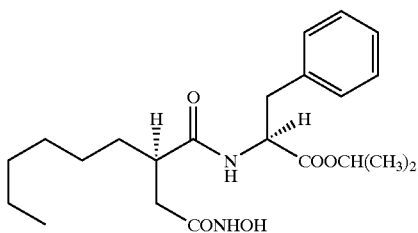

The title compound was prepared using procedures analogous to those described for example 7, starting with 2R-n-hexylsuccinic acid 4-tert-butyl ester and L-phenylalanine isopropyl ester hydrochloride. $^1$H-NMR δ (methanol-d$_4$), 7.19–7.09 (5H, m), 4.85–4.75 (1H, m), 4.50 (1H, dd, J=8.2, 6.9 Hz), 2.99 (1H, dd, J=13.7, 6.7 Hz), 2.86 (1H, dd, J=13.7, 8.3 Hz), 2.68–2.52 (1H, m), 2.03–1.92 (2H, m), 1.48–1.25 (1H, m), 1.16–1.11 (9H, m), 1.10 (3H, d, J=6.3 Hz), 1.01 (3H, d, J=6.3 Hz) and 0.78 (3H, t, J=6.2 Hz). $^{13}$C-NMR; δ (methanol-d$_4$), 177.1, 172.5, 170.4, 138.2, 130.4, 129.5, 127.8, 70.1, 55.4, 43.7, 38.5, 36.4, 33.1, 32.8, 30.4, 28.1, 23.6, 22.0, 21.9 and 14.4.

EXAMPLE 11

2S-[2R-(S-Hydroxy-hydroxycarbamoyl-methyl)-4-methyl-pentanoylamino]-3-phenyl-propionic acid cyclopentyl ester

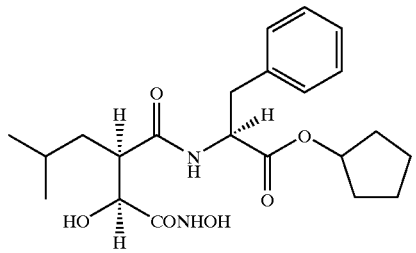

(a) 2S-[2R-(2,2-Dimethyl-5-oxo-[1,3]dioxolan-4S-yl)-4-methyl-pentanoylamino]-3-phenylpropionic acid cyclopentyl ester.

A solution of 2R-(2,2-dimethyl-5-oxo-[1,3-dioxolan-4S-yl)-4-methyl-pentanoic acid pentafluorophenyl ester (WO95/19956) (1.93 g, 4.9 mmol) and L-phenylalanine cyclopentyl ester (1.16 g, 5.0 mmol) in ethyl acetate (50 mL) was heated under reflux for 2 hours. The reaction mixture was diluted with ethyl acetate and washed with 1M aqueous sodium carbonate, 1M hydrochloric acid and brine before drying over magnesium sulphate, filtration and concentration under reduced pressure. The product was purified by column chromatography on silica gel eluting with 5% methanol/DCM. Product containing fractions were combined and concentrated under reduced pressure to leave 2S-[2R-(2,2-dimethyl-5-oxo-[1,3]-dioxolan-4S-yl)-4-methyl-pentanoylamino]-3-phenylpropionic acid cyclopentyl ester as a white solid (305 mg, 28%). $^1$H-NMR: δ (CDCl$_3$), 7.32–7.15 (5H, m), 6.42 (1H, d, J=7.5 Hz), 5.21–5.15 (1H, m), 4.87–4.80 (1H, m), 4.50 (1H, d, J=5.9 Hz), 3.11–3.08 (2H, m), 2.73–2.65 (1H, m), 1.83–1.55 (11H, m), 1.58 (3H, s), 1.53 (3H, s), 0.89 (3H, d, J=6.0 Hz) and 0.88 (3H, d, J=6.1 Hz).

(b) 2S-[2R-(S-Hydroxy-hydroxycarbamoyl-methyl)-4-methyl-pentanoylamino]-3-phenyl-propionic acid cyclopentyl ester.

A solution of sodium methoxide (100 mg, 1.9 mmol) in methanol (3 mL) was treated with hydroxylamine hydrochloride (122 mg, 1.9 mmol) and allowed to stir at room temperature for 2 hours. The solution of methanolic hydroxylamine was then filtered into a solution of 2S-[2R-(2,2-dimethyl-5-oxo-[1,3]-dioxolan-4S-yl)-4-methyl-pentanoylamino]-3-phenylpropionic acid cyclopentyl ester in methanol (10 mL). The reaction was allowed to stir at room temperature for 18 hours. The reaction mixture was concentrated under reduced pressure and the residue redissolved in ethyl acetate. The solution was washed with 1M hydrochloric acid and brine, dried over magnesium sulphate, filtered and concentrated under reduced pressure. Recrystallisation from ethyl acetate/hexane provided 2S-[2R-(S-hydroxy-hydroxycarbamoyl-methyl)-4-methyl-pentanoylamino]-3-phenyl-propionic acid cyclopentyl ester as a white solid (55 mg, 18%). $^1$H-NMR; δ (methanol-d$_4$), 8.23 (1H, d, J=7.3 Hz, 7.20–7.09 (5H, m), 5.99–5.95 (1H, m), 4.53 (1H, dd, J=14.6, 7.3 Hz), 3.88 (1H, d, J=7.0 Hz), 2.94 (2H, d, J=7.4 Hz), 2.73–2.64 (1H, m), 1.80–1.30 (10H, m), 1.09–1.01 (1H, m), 0.81 (3H, d, J=6.5 Hz) and 0.76 (3H, d, J=6.4 Hz). $^{13}$C-NMR; δ (methanol-d$_4$), 175.8, 172.8, 171.6, 138.0, 130.4, 129.5, 127.9, 79.6, 73.2, 55.4, 49.2, 39.1, 38.7, 33.5, 26.7, 24.6, 24.0 and 22.1

EXAMPLE 12

2S-(3S-Hydroxycarbamoyl-2R-isobutyl-hex-5-enoylamino)-3S-methyl-pentanoic acid cyclopentyl ester

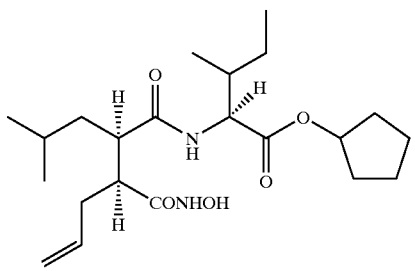

(a) N-Benzyloxycarbonyl-L-isoleucine cyclopentyl ester.

A solution of N-benzyloxycarbonyl-L-isoleucine (10.0 g, 37.7 mmol) in DCM (150 mL) was treated with N-(3-dimethylaminopropyl)-N'-ethylcarbodiimide hydrochloride (7.94 g, 41.5 mmol), cyclopentanol (3.90 g, 45.2 mmol) and N,N-dimethylaminopyridine (20 mg). The reaction was allowed to stand at room temperature for 18 hours. The reaction mixture was washed with 1M hydrochloric acid, saturated sodium bicarbonate, and brine before drying over magnesium sulphate, filtration and removal of solvent under reduced pressure to leave N-benzyloxycarbonyl-L-isoleucine cyclopentyl ester as a colourless ester as a colourless oil (10.99 g, 87%). $^1$H-NMR; δ (CDCl$_3$) 7.44–7.30 (5H, m), 5.37–5.34 (1H, m), 5.22–5.18 (1H, m), 5.11 (2H, s), 4.33–4.27 (1H, m), 1.90–1.55 (10H, m), 1.51–1.35 (1H, m), 1.28–1.20 (2H, m), 0.93 (3H, d, J 6.9 Hz) and 0.91 (3H, d, J=7.0 Hz).

(b) 2S-(3S-Hydroxycarbamoyl-2R-isobutyl-hex-5-enoylamino)-3S-methyl-pentanoic acid cyclopentyl ester.

N-Benzyloxycarbonyl-L-isoleucine cyclopentyl ester was converted to the title compound using chemistry analogous to that described for example 6. $^1$H-NMR; δ (methanol-d$_4$), 8.40 (1H, d, J=7.9 Hz), 5.64–5.47 (1H, m), 5.09–5.04 (1H, m), 4.93–4.85 (2H, m), 4.25–4.19 (1H, m), 2.56–2.49 (1H, m), 2.24–2.04 (2H, m), 1.98–1.88 (1H, m), 1.79–1.18 (12H, m), 1.22–1.10 (1H, m), 1.00–0.96 (1H, m) and 0.95–0.73 (12H, m). $^{13}$C-NMR; δ (methanol-d$_4$), 176.6, 172.6, 172.4, 165.9, 142.3, 136.0, 117.5, 79.3, 58.5, 47.7, 41.7, 37.9, 33.5, 26.8, 26.5, 24.6, 24.5, 21.8, 16.0 and 11.4.

EXAMPLE 13

2S-(3S-Hydroxycarbamoyl-2R-isobutyl-hex-5-enoylamino)-3-phenylpropionic acid 2-methoxy-ethyl ester

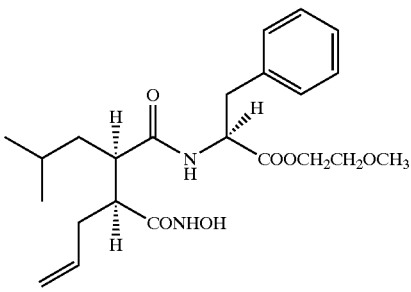

(a) N-(Carbobenzyloxy)-L-phenylalanine 2-methoxy-ethyl ester.

A solution of N-(carbobenzyloxy)-L-phenylalanine (10.0 g, 33.4 mmol) in DMF (75 mL) was treated with HOBT (6.8 g, 50.1 mmol), N-(3-dimethylaminopropyl)-N'-ethylcarbodiimide hydrochloride (7.7 g, 40.1 mmol), 2-methoxyethanol (2.8 g, 36.8 mmol) and a catalytic amount of 4-N,N-dimethylaminopyridine. The reaction mixture was stirred overnight at room temperature. The reaction mixture was concentrated under reduced pressure and the residue taken up in ethyl acetate and washed with 1M hydrochloric acid, saturated sodium hydrogen carbonate and brine. The solution was dried over sodium sulphate, filtered and concentrated under reduced pressure to provide N-(carbobenzyloxy)-L-phenylalanine 2-methoxy-ethyl ester as a yellow foam (8.8 g, 74%). $^1$H-NMR; δ (CDCl$_3$), 7.44–7.12 (10H, m), 5.27 (1H, d), 5.11 (2H, s), 4.72 (1H, dd), 4.26 (2H, m), 3.57 (2H, t), 3.38 (3H, s) and 3.15 (2H, m).

(b) L-Phenylalanine 2-methoxy-ethyl ester.

A solution of N-(carbobenzyloxy)-L-phenylalanine 2-methoxy-ethyl ester (4.4 g, 12.3 mmol) in ethanol (75 mL) was treated with palladium on charcoal catalyst (440 mg, 10% Pd on charcoal) as a slurry in ethyl acetate (10 mL). Hydrogen gas was passed through the suspension for 3 hours. The reaction mixture was filtered and concentrated under reduced pressure to provide L-phenylalanine 2-methoxy-ethyl ester as a colourless oil (2.5 g, 92%). $^1$H-NMR; d (methanol-d$_4$), 7.35–7.20 (5H, m), 4.27 (2H, m), 3.79 (1H, m), 3.57 (2H, m), 3.38 (3H, s), 3.10 (1H, dd), 2.90 (1H, dd) and 1.64 (2H, s).

(c) 2S-{1R-[1S-(2-Methoxy-ethoxycarbonyl)-2-phenyl-ethylcarbamoyl]-3-methyl-butyl}-pent-4-enoic acid tert-butyl ester.

A solution of L-phenylalanine 2-methoxy-ethyl ester (910 mg, 4.1 mmol) in DMF (15 mL) was treated with 3S-tert-butoxycarbonyl-2R-isobutyl-hex-5-enoic acid (1.0 g, 3.7 mmol), HOBT (750 mg, 5.6 mmol), N-(3-dimethylaminopropyl)-N'-ethylcarbodiimide hydrochloride (850 mg, 4.4 mmol) and NMM (560 mg, 5.6 mmol). The reaction was stirred overnight at room temperature. The reaction mixture was concentrated under reduced pressure and the residue taken up in ethyl acetate. The solution was washed with 1M hydrochloric acid, saturated sodium hydrogen carbonate and brine. The solution was dried over sodium sulphate, filtered and concentrated under reduced pressure. The product was purified by column chromatography, eluting with 1–2% methanol/DCM. Product-containing fractions were combined and concentrated under reduced pressure to provide 2S-{1R-[1S-(2-methoxy-ethoxycarbonyl)-2-phenyl-ethylcarbamoyl]-3-methyl-butyl}-pent-4-enoic acid tert-butyl ester as an off-white gum (1.0 g, 58%). ¹H-NMR; δ (CDCl₃), 7.32–7.17 (5H, m), 6.00 (1H, d), 5.65 (1H, m), 4.98 (3H, m), 4.28 (2H, m), 3.56 (2H, m), 3.38 (3H, s), 3.20 (1H, dd), 3.07 (1H, dd), 2.45 (1H, m), 2.35 (1H, m), 1.97 (1H, m), 1.65 (1H, m), 1.49 (1H, m), 1.42 (9H, s), 1.06 (1H, m) and 0.85 (6H, 2×d).

(d) 2S-(3S-Hydroxycarbonyl-2R-isobutyl-hex-5-enoylamino)-3-phenylpropionic acid 2-methoxy-ethyl ester.

A solution of 2S-{1R-[1S-(2-methoxy-ethoxycarbonyl)-2-phenyl-ethylcarbamoyl]-3-methyl-butyl}-pent-4-enoic acid tert-butyl ester (1.0 g, 2.1 mmol) in a mixture of TFA and DCM (1:1, 6 mL) was allowed to stand at 5° C. overnight. The reaction mixture was concentrated under reduced pressure and azeotroped with toluene. Crystallisation of the product from ethyl acetate/hexane gave 2S-(3S-hydroxycarbonyl-2R-isobutyl-hex-5-enoylamino)-3-phenylpropionic acid 2-methoxy-ethyl ester as a white solid (387 mg, 44%). ¹H-NMR; δ (CDCl₃), 7.33–7.13 (5H, m), 6.22 (1H, d), 5.65 (1H, m), 5.08–4.94 (3H, m), 4.38–4.24 (2H, m), 3.61 (2H, m), 3.40 (3H, s), 3.26 (1H, dd), 3.09 (1H, dd), 2.55 (1H, m), 2.41 (2H, m), 2.03 (1H, m), 1.66 (1H, dt), 1.49 (1H, m), 1.16 (1H, m) and 0.86 (6H, 2×d).

(e) 2S-(3S-Hydroxycarbamoyl-2R-isobutyl-hex-5-enoylamino)-3-phenylpropionic acid 2-methoxy-ethyl ester.

A solution of 2S-(3S-hydroxycarbonyl-2R-isobutyl-hex-5-enoylamino)-3-phenylpropionic acid 2-methoxy-ethyl ester (375 mg, 0.9 mmol) in DMF (5 mL) was cooled in an ice/water bath. N-(3-Dimethylaminopropyl)-N'-ethylcarbodiimide hydrochloride (205 mg, 117 mmol) and HOBT (145 mg, 1.1 mmol) were added with stirring. After 2 hours at this temperature, a solution of hydroxylamine hydrochloride (93 mg, 1.3 mmol) and NMM (136 mg, 1.3 mmol) in DMF (5 mL) was added. The reaction was allowed to warm to room temperature and stirred overnight. The reaction mixture was concentrated under reduced pressure and the residue partitioned between ethyl acetate and water. The organic phase was washed with 5% aqueous sodium carbonate and water, dried over sodium sulphate, filtered and concentrated under reduced pressure. The product was recrystallised from ethyl acetate/hexane to yield 2S-(3S-hydroxycarbamoyl-2R-isobutyl-hex-5-enoylamino)-3-phenylpropionic acid 2-methoxy-ethyl as a white solid (185 mg, 48%). ¹H-NMR; δ (methanol-d₄), 7.20–7.05 (5H, m), 5.33 (1H, m), 4.79–4.67 (4H, m), 4.15 (2H, m), 3.48 (2H, m), 3.25 (3H, s), 3.15 (1H, m), 2.80 (1H, dd, J=10.9, 13.9 Hz), 2.37 (1H, dt, J=11.1, 3.2 Hz), 1.90 (1H, dt, J=11.4, 3.4 Hz), 1.77 (1H, m), 1.44–1.18 (3H, bm), 0.91 (1H, m), 0.79 (3H, d, J=6.4 Hz) and 0.72 (3H, d, J=6.5 Hz). ¹³C-NMR; δ (methanol-d₄) 176.4, 172.8, 138.3, 136.1, 130.3, 129.5, 128.0, 117.3, 71.3, 65.2, 59.1, 55.0, 47.9, 41.6, 38.2, 35.7, 26.6, 24.6 and 21.6.

EXAMPLE 14

2S-[2R-(1S-Hydroxycarbamoyl-ethyl)-4-methyl-pentanoylamino]-3-phenyl-propionic acid 2-methoxy-ethyl ester

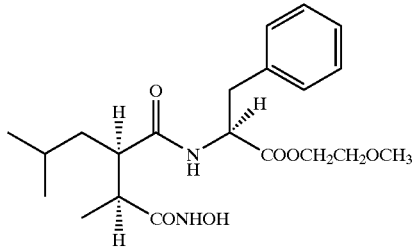

(a) 2-{1R-[1S-(2-Methoxy-ethoxycarbonyl)-2-phenyl-ethylcarbamoyl]-3-methyl-butyl}-malonic acid dibenzyl ester.

A solution of 2-benzyloxycarbonyl-3R-isobutyl succinic acid 1-benzyl ester (4.06 g, 10.2 mmol), L-phenylalanine 2-methoxy-ethyl ester (see Example 13, 2.50 g, 11.2 mmol), HOBT (2.06 g, 15.3 mmol), N-methylmorpholine (1.54 g, 15.3 mmol) and N-(3-dimethylaminopropyl)-N'-ethylcarbodiimide hydrochloride (2.34 g, 12.2 mmol) in DMF (25 mL) was stirred at room temperature for 18 hours. The reaction mixture was concentrated under reduced pressure, the residue taken up in ethyl acetate and washed with 1M citric acid, saturated sodium hydrogen carbonate and brine. The solution was dried with sodium sulphate, filtered and concentrated under reduced pressure. The product was purified by column chromatography, eluting with 2–3% methanol/DCM. Product-containing fractions were combined and concentrated under reduced pressure to provide 2-{1R-[1S-(2-methoxy-ethoxycarbonyl)-2-phenyl-ethylcarbamoyl]-3-methyl-butyl}-malonic acid dibenzyl ester (4.89 g,80%). ¹H NMR; δ (CDCl₃), 7.39–7.13 (15H, bm), 6.30 (1H, d), 5.13 (3H, m), 4.90 (1H, m), 4.23 (2H, m), 3.86 (1H, d), 3.48 (3H, m), 3.35 (3H, s), 3.14 (1H, dd), 2.96 (2H, m), 1.68–1.45 (2H, m), 1.00 (1H, m), 0.78 (3H, d) and 0.77 (3H, d).

(b) 2-{1R-[1S-(2-Methoxy-ethoxycarbonyl)-2-phenyl-ethylcarbamoyl]-3-methyl-butyl}-acrylic acid.

A solution of 2-{1R-[1S-(2-methoxy-ethoxycarbonyl)-2-phenyl-ethylcarbamoyl]-3-methyl-butyl}-malonic acid dibenzyl ester (4.88 g, 8.1 mmol) in ethanol (25 mL) was treated with palladium catalyst (490 mg, 10% Pd/charcoal) as a slurry in ethyl acetate (5 mL). Hydrogen gas was passed through the suspension for 2 hours. The reaction mixture was filtered and treated with piperidine (830 mg, 9.7 mmol) and formaldehyde (as a 37 weight percent solution in water, 0.79 mL, 9.7 mmol). The solution was allowed to stand at room temperature for 18 hours. The reaction mixture was concentrated under reduced pressure and the residue resuspended in ethyl acetate. The solution was washed with saturated sodium hydrogen carbonate. The aqueous phase was acidified to pH 1 with 1M hydrochloric acid and extracted with ethyl acetate. The organic phase was dried over sodium sulphate, filtered and concentrated under reduced pressure to provide 2-{1R-[1S-(2-methoxy-ethoxycarbonyl)-2-phenyl-ethylcarbamoyl]-3-methyl-butyl}-acrylic acid as a waxy white solid (2.21 g, 70%). ¹H NMR; δ (CDCl₃), 7.27–7.06 (5H, bm), 6.50 (1H, d), 6.43 (1H, s), 5.85 (1H, s), 4.92 (2H, m), 4.29 (2H, m), 3.59 (2H, t), 3.48 (1H, m), 3.39 (3H, s), 3.12 (2H, m), 1.79 (1H, m), 1.51 (2H, m), 0.90 (3H, d) and 0.87 (3H, d).

(c) 3R-[1S-(2-Methoxy-ethoxycarbonyl)-2-phenyl-ethylcarbamoyl]-2S,5-dimethyl-hexanoic acid.

A solution of 2-{1R-[1S-(2-methoxy-ethoxycarbonyl)-2-phenyl-ethylcarbamoyl]-3-methyl-butyl}-acrylic acid (2.21 g, 5.65 mmol) in ethanol (40 mL) was treated with palladium catalyst (220 mg, 10% Pd/charcoal) as a slurry in ethyl acetate (5 mL). Hydrogen gas was passed through the suspension for 4 hours. The reaction mixture was filtered and concentrated under reduced pressure to provide 3R-[1S-(2-methoxy-ethoxycarbonyl)-2-phenyl-ethylcarbamoyl]-2S,5-dimethyl-hexanoic acid (1.96 g, 88%). $^1$H NMR; δ (CDCl$_3$), 7.31–7.14 (5H, m), 6.49 (1H, d), 5.55 (1H, bs), 4.98 (1H, m), 4.27 (2H, m), 3.57 (2H, m), 3.37 (3H, s), 3.19 (1H, dd), 3.07 (1H, m), 2.57 (1H, t), 2.44 (1H, m), 1.71–1.42 (2H, m), 1.11 (1H, m), 1.00 (2H, d), 0.85 (3H, d) and 0.84 (3H, d).

(d) 2S-[2R-(1S-Benzyloxycarbamoyl-ethyl)-4-methyl-pentanoylamino]-3-phenyl-propionic acid 2-methoxy-ethyl ester.

A solution of 3R-[1S-(2-methoxy-ethoxycarbonyl)-2-phenyl-ethylcarbamoyl)-2S,5-dimethyl-hexanoic acid (1.96 g, 5.0 mmol) in DMF (30 mL) was treated with HOBT (810 mg, 6.0 mmol), O-benzylhydroxylamine (740 mg, 6.0 mmol) and N-(3-dimethylaminopropyl)-N'-ethylcarbodiimide hydrochloride (1.15 g, 6.0 mmol) and stirred at ambient temperature for 48 hours. The reaction mixture was concentrated under reduced pressure and the residue dissolved in ethyl acetate. The solution was washed with 1M hydrochloric acid, saturated sodium hydrogen carbonate and brine. The solution was dried with sodium sulphate, filtered and concentrated under reduced pressure. The product was recrystallised from ethyl acetate/hexane to provide 2S-[2R-(1S-benzyloxycarbamoyl-ethyl)-4-methyl-pentanoylamino]-3-phenyl-propionic acid 2-methoxy-ethyl ester as a white solid (1.63 g, 66%). $^1$H NMR; δ (CDCl$_3$), 9.21 (1H, s), 7.41–7.14 (10H, m), 6.37 (1H, d), 4.91 (3H, s), 4.27 (2H, m), 3.56 (2H, t), 3.36 (3H, s), 3.18 (1H, dd), 3.05 (1H, dd), 2.44 (1H, m), 2.18 (1H, m), 1.78 (1H, s), 1.47 (2H, m), 1.04 (1H, m), 0.85 (3H, d and 0.81 (3H, d).

(e) 2S-[2R-(1S-Hydroxycarbamoyl-ethyl)-4-methyl-pentanoylamino]-3-phenyl-propionic acid 2-methoxy-ethyl ester.

A solution of 2S-[2R-(1S-benzyloxycarbamoyl-ethyl)-4-methyl-pentanoylamino]-3-phenyl-propionic acid 2-methoxy-ethyl ester (1.62 g, 3.3 mmol) in ethanol (30 mL) was treated with palladium catalyst (160 mg, 10% Pd/charcoal) as a slurry in ethyl acetate (5 mL). Hydrogen gas was passed through the suspension for 2 hours. The reaction mixture was filtered and concentrated under reduced pressure. The product was recrystallised from ethyl acetate/hexane to provide 2S-[2R-(1S-hydroxycarbamoyl-ethyl)-4-methyl-pentanoylamino]-3-phenyl-propionic acid 2-methoxy-ethyl ester as a white solid (942 mg, 71%). $^1$H-NMR; δ (methanol-d$_4$), 7.16–7.06 (5H, m), 4.70 (1H, m), 4.14 (2H, t, J=4.7 Hz), 3.47 (2H, m), 3.25 (3H, s), 3.18 (1H, m), 2.82 (1H, dd, J=10.5, 13.9 Hz), 2.34 (1H, m), 1.94 (1H, m), 1.40 (2H, m), 0.89 (1H, m), 0.89 (1H, m), 0.78 (3H, d, J=6.4 Hz), 0.72 (3H, d, J=6.4 Hz) and 0.48 (3H, d, J=6.8 Hz). $^{13}$C-NMR; δ (methanol-d$_4$), 176.6, 174.4, 172.8, 138.4, 130.3, 129.5, 127.8, 78.8, 71.3, 65.2, 59.1, 55.1, 48.6, 42.0, 41.7, 36.3, 26.8, 24.6, 21.7 and 16.5.

EXAMPLE 15

2S-(3S-Hydroxycarbamoyl-2R-isobutyl-hexanoylamino)-3,3-dimethyl-butyric acid 2-methoxy-ethyl ester

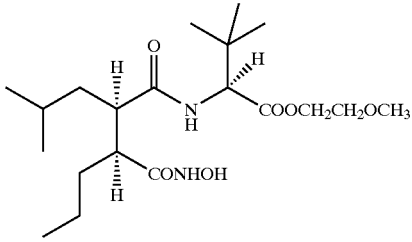

(a) 2S-{1R-[1S-(2-Methoxy-ethoxycarbonyl)-2,2-dimethyl-propylcarbamoyl]-3-methyl-butyl}-pent-4-enoic acid tert-butyl ester.

L-tert-Leucine 2-methoxy-ethyl ester (840 mg, 4.4 mmol), which had been prepared in a similar way to L-phenylalanine 2-methoxy-ethyl ester (example 13) was dissolved in DMF (15 mL). This solution was treated with 3S-tert-butoxycarbonyl-2R-isobutyl-hex-5-enoic acid (1.09 g, 4.0 mmol), HOBT (820 mg, 6.1 mmol), NMM (610 mg, 6.1 mmol) and N-(3-dimethylaminopropyl)-N'-ethylcarbodiimide hydrochloride (930 mg, 4.9 mmol) and stirred at ambient temperature for 18 hours. The reaction mixture was concentrated under reduced pressure and the residue taken up in ethyl acetate. The solution was washed with 1M hydrochloric acid, saturated sodium hydrogen carbonate and brine. The organic phase was dried with sodium sulphate, filtered and concentrated under reduced pressure. The product was purified by column chromatography, eluting with 1% methanol/DCM. Product-containing fractions were combined and concentrated under reduced pressure to provide 2S-{1R-[1S-(2-methoxy-ethoxycarbonyl)-2,2-dimethyl-propylcarbamoyl]-3-methyl-butyl}-pent-4-enoic acid tert-butyl ester as an off-white solid (1.02 g, 57%). $^1$H NMR; δ(CDCl$_3$), 6.14 (1H, d), 5.73 (1H, m), 5.04 (2H, m), 4.48 (1H, d), 4.28 (2H, m), 3.59 (2H, t), 3.36 (3H, s), 2.49 (3H, m), 2.26 (2H, m), 1.68 (1H, m), 1.47 (9H, m), 1.12 (2H, m), 1.09 (9H, s) 0.90 (3H, d) and 0.86 (3H, d).

(b) 2S-{1R-[1S-(2-Methoxy-ethoxycarbonyl)-2,2-dimethyl-propylcarbamoyl]-3-methyl-butyl}-pent-4-enoic acid A solution of 2S-{1R-[1S-(2-methoxy-ethoxycarbonyl)-2,2-dimethyl-propylcarbamoyl]-3-methyl-butyl}-pent-4-enoic acid tert-butyl ester (100 g, 2.3 mmol) in a mixture of TFA and DCM (1:1, 6 mL) was allowed to stand at 5° C. overnight. The reaction mixture was concentrated under reduced pressure and azeotroped with ethyl acetate and toluene to leave 2S-{1R-[1S-(2-methoxy-ethoxycarboyl)-2,2-dimethyl-propylcarbamoyl]-3-methyl-butyl}-pent-4-enoic acid as a yellow gum (870 mg, quantitative). $^1$H-NMR; δ(methanol-d$_4$), 8.21 (1H, d), 5.64 (1H, m), 4.92 (3H, m), 4.26 (1H, d), 4.14 (2H, m), 3.49 (2H, m), 3.24 (3H, s), 2.67 (1H, m), 2.44 (1H, m), 2.16 (3H, m), 1.60–1.32 (3H, m), 1.02 (1H, m), 0.91 and 0.77 (6H, m).

(c) 2S-(3S-Benzyloxycarbamoyl-2R-isobutyl-hex-5-enoylamino)-3,3-dimethyl-butyric acid 2-methoxy-ethyl ester.

A solution of 2S-{1R-[1S-(2-methoxy-ethoxycarbonyl)-2,2-dimethyl-propylcarbamoyl]-3-methyl-butyl}-pent-4- enoic acid (463 mg, 1.2 mmol) in DMF (5 mL) was treated with HOBT (195 mg, 1.4 mmol), N-(3-dimethylaminopropyl)-N'-ethylcarbodiimide hydrochloride (276 mg, 1.4 mmol) and O-benzylhydroxylamine (177 mg, 1.4 mmol). The reaction was stirred at ambient temperature for 18 hours. The reaction mixture was concentrated under reduced pressure and taken up in ethyl acetate. The solution was washed with 1M hydrochloric acid, saturated sodium hydrogen carbonate and brine. The organic phase was dried with sodium sulphate, filtered and concentrated under reduced pressure. The product was recrystallized from ethyl acetate/hexane to provide 2S-(3S-benzyloxycarbamoyl-2R-isobutyl-hex-5-enoylamino)-3,3-dimethyl-butyric acid 2-methoxy-ethyl ester as a while solid (106 mg, 18%). $^1$H-NMR; δ(CDCl$_3$), 9.03 (1H, s), 7.42–7.34 (5H, m), 6.26 (1H, d), 5.65 (1H, m), 4.97 (4H, m), 4.42 (1H, d), 4.28 (2H, m), 3.58 (2H, t), 3.35 (3H, s), 2.57–2.26 (4H, m), 1.47 (2H, m), 1.11 (1H, m), 1.00 (9H, m), 0.89 (3H, d) and 0.83 (3H, d).

(d) 2S-(3S-Hydroxycarbamoyl-2R-isobutyl-hexanoylamino)-3,3-dimethyl-butyric acid 2-methoxy-ethyl ester.

A solution of 2S-(3S-benzyloxycarbamoyl-2R-isobutyl-hex-5-enoylamino)-3,3-dimethyl-butyric acid 2-methoxy-ethyl ester (95 mg, 0.2 mmol) in ethanol (20 mL) was treated with palladium catalyst (10 mg, 10% Pd/charcoal) as a slurry in ethyl acetate (3 mL). Hydrogen gas was passed through the suspension for 4 hours. The reaction mixture was filtered and concentrated under reduced pressure. The product was purified by preparative HPLC using a C18 silica column, eluting with 70% methanol/30% water (containing 0.1% TFA). Product-containing fractions were combined and concentrated under reduced pressure. The product was dissolved in DCM and washed with saturated sodium hydrogen carbonate. The organic solution was dried with sodium sulphate, filtered and concentrated under reduced pressure to provide 2S-(3S-hydroxycarbamoyl-2R-isobutyl-hexanoylamino)-3,3-dimethyl-butyric acid 2-methoxy-ethyl ester as a white solid (40 mg, 52%). $^1$H-NMR; δ(methanol-d$_4$), 8.28 (1H, J=8.7 Hz), 4.27 (1H, J=8.8 Hz), 4.14 (2H, m), 3.49 (2H, t, J=4.7 Hz), 3.24 (3H, s), 2.57 (1H, dt, J=10.9, 3.1 Hz), 2.07 (1H, m), 1.50–0.99 (7H, bm), 0.95 (9H, s) and 0.91–0.72 (9H, m). $^{13}$C-NMR; δ(methanol-d$_4$), 177.0, 173.2, 172.2, 71.4, 64.6, 62.6, 62.5, 58.9, 47.9, 47.8, 41.8, 34.9, 34.3, 27.3, 26.8, 24.5, 21.8, 21.5 and 14.3.

EXAMPLE 16

2S-[2R-(S-Hydroxycarbamoyl-methoxy-methyl)-4-methyl-pentanoylamino]-3-phenyl-propionic acid isopropyl ester

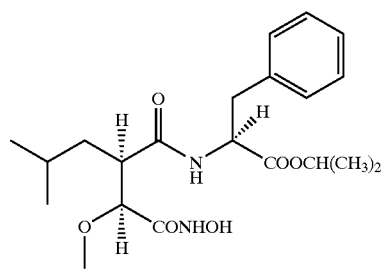

(a) 2R-(S-Benzyloxycarbamoyl-methoxy-methyl)-4-methyl-pentanoic acid.

A solution of 3R-isobutyl-4S-methoxy-dihydrofuran-2,5-dione (WO 97/02239) (609 mg, 3.27 mmol), and O-benzylhydroxylamine (403 mg, 3.27 mmol) in ethyl acetate (5 mL) was stirred at room temperature for 1 hour. The reaction mixture was concentrated under reduced pressure to provide 2R-(S-benzyloxycarbamoyl-methoxy-methyl)-4-methyl-pentanoic acid as a white foam (1.01 g, 100%). $^1$H NMR; δ(CDCl$_3$), 7.43–7.36 (5H, m), 5.00–4.89 (2H, m), 3.90 (1H, d, J=6.0 Hz), 3.34 (3H, s), 2.91–2.84 (1H, m), 1.74–1.65 (2H, m), 1.35–1.24 (1H, m), 0.94–0.89 (6H, 2 xd).

(b) 2S-[2R-(S-Benzyloxycarbamoyl-methoxy-methyl)-4-methyl-pentanoylamino]-3-phenyl-propionic acid isopropyl acid isopropyl ester.

A solution of 2R-(S-benzyloxycarbamoyl-methoxy-methyl)-4-methyl-pentanoic acid (1.01 g, 3.3 mmol) in tetrahydrofuran (15 mL) at 0° C. was treated with L-phenylalanine isopropyl ester (810 mg, 3.9 mmol) and N-(3-dimethylaminopropyl)-N'-ethylcarbodiimide hydrochloride (750 mg, 3.9 mmol). The reaction mixture was allowed to warm to ambient temperature and stirred for 18 hours. The solution was concentrated under reduced pressure and the residue taken up in DCM. This solution was washed with 1M hydrochloric acid, saturated sodium hydrogen carbonate and brine. The organic phase was dried with sodium sulphate, filtered and concentrated under reduced pressure. The product was purified by column chromatography, eluting with 2% methanol/DCM. Product-containing fractions were combined and concentrated under reduced pressure to provide 2S-[2R-(S-benzyloxycarbamoyl-methoxy-methyl)-4-methyl-pentanoylamino]-3-phenyl-propionic acid isopropyl ester as a white solid (1.39 g, 85%). $^1$H NMR; δ(methanol-d$_4$), 7.34–7.08 (10H, m), 4.83 (1H, m), 4.79 (2H, s), 4.58 (1H, m), 3.32 (1H, d), 3.00 (1H, m), 2.94 (3H, s), 2.86 (1H, m), 2.59 (1H, m), 1.36 (2H, m), 1.14 (1H, m), 1.07 (6H, dd), 0.77 (3H, d) and 0.72 (3H, d).

(c) 2S-[2R-(S-Hydroxycarbamoyl-methoxy-methyl)-4-methyl-pentanoylamino]-3-phenyl-propionic acid isopropyl ester.

A solution of 2S-[2R-(S-benzyloxycarbamoyl-methoxy-methyl)-4-methyl-pentanoylamino]-3-phenyl-propionic acid isopropyl ester (1.37 g, 2.8 mmol) in ethanol (30 mL) was treated with palladium catalyst (274 mg, 10%Pd/charcoal) as a slurry in ethyl acetate (5 mL). Hydrogen gas was passed through the suspension for 2 hours. The reaction mixture was filtered and concentrated under reduced pressure. The product was recrystallized from ethyl acetate to provide 2S-[2R-(S-hydroxycarbamoyl-methoxy-methyl)-4-methyl-pentanoylamino]-3-phenyl-propionic acid isopropyl ester as a white solid (778 mg, 70%). $^1$H-NMR; δ(methanol-d$_4$), 7.12 (5H, m), 4.85 (1H, m), 4.59 (1H, dd, J=8.2, 6.2 Hz), 3.39 (1H, d, J=9.7 Hz), 3.02 (3H, s), 2.92 (2H, m), 2.63 (1H, dt, J=11.1, 3.4 Hz), 1.44 (2H, m), 1.11 (3H, d, J=6.2 Hz), 1.03 (3H, d, J=6.3 Hz), 0.87 (1H, m), 0.80 (3H, d, J=6.4 Hz) and 0.75 (3H, d, J=6.4 Hz). $^{13}$C-NMR; δ(methanol-d$_4$), 175.3, 172.4, 169.4, 138.2, 130.3, 129.4, 127.7, 82.8, 70.1, 58.0, 55.4, 48.7, 38.4, 26.5, 24.3, 22.0, 21.9, and 21.8.

EXAMPLE 17

2S-{2R-[1S-Hydroxycarbamoyl-2-(thiophen-2-ylsulphanyl)-ethyl]-4-methyl-pentanoylamino}-3-phenyl-propionic acid isopropyl ester

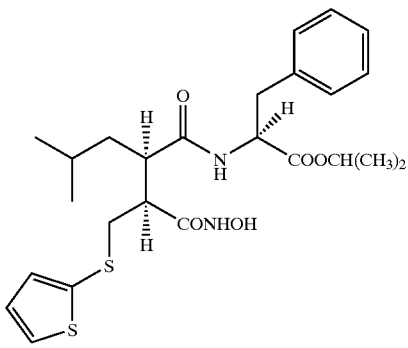

(a) 3R-(1S-Isopropoxycarbonyl-2-phenyl-ethylcarbamoyl)-5-methyl-2S-(thiophen-2-ylsulphanylmethyl)-hexanoic acid.

A solution of 2-[1R-(1S-isopropoxycarbonyl-2-phenyl-ethylcarbamoyl)-3-methyl-butyl]-acrylic acid (intermediate in example 5) (1.67 g, 4.5 mmol) in propan-2-ol (5 mL) was treated with 2-mercaptothiophene (1.03 g, 8.9 mmol). The reaction mixture was heated at 60° C. in the dark for 72 hours. The solution was concentrated under reduced pressure. The product was purified by column chromatography, eluting with 1% methanol/DCM. Product-containing fractions were combined and concentrated under reduced pressure to provide 3R-(1S-isopropoxycarbonyl-2-phenyl-ethylcarbamoyl)-5-methyl-2S-(thiophen-2-ylsulphanylmethyl)-hexanoic acid as an off-white foam (1.08 g, 49%). $^1$H NMR; δ(CDCl$_3$), 7.36–7.27 (4H, m), 7.18 (2H, m), 7.05 (1H, m), 7.00 (1H, m), 6.35 (1H, d), 5.07 (1H, m), 4.85 (1H, m), 3.23 (2H, m), 3.08 (1H, dd), 2.79–2.59 (3H, m), 1.59 (2H, m), 1.25 (6H, t), 1.17 (1H, m) and 0.86 (6H, 2 xd).

(b) 2S-{2R-[1S-Hydroxycarbamoyl-2-(thiophen-2-ylsulphanyl)-ethyl]-4-methyl-pentanoylamino}-3-phenyl-propionic acid isopropyl ester.

A solution of 3R-(1S-isopropoxycarbonyl-2-phenyl-ethylcarbamoyl)-5-methyl-2S-(thiophen-2-ylsulphanylmethyl)-hexanoic acid (1.06 g, 2.2 mmol) in DMF (6 mL) was treated with HOBt (350 mg, 2.6 mmol) and N-(3-dimethylaminopropyl)-N'-ethylcarbodiimide hydrochloride (497 mg, 2.6 mmol). The solution was stirred in an ice/water bath for 2 hours and then treated with a pre-mixed solution of hydroxylamine hydrochloride (225 mg, 3.2 mmol) and NMM (328 mg, 3.2 mmol) in DMF (5 mL). The reaction mixture was stirred at ambient temperature for 96 hours. The solution was concentrated under reduced pressure and the residue taken up in ethyl acetate and partitioned with water. The organic phase was washed with 0.5M sodium carbonate and water, dried with sodium sulphate, filtered and concentrated under reduced pressure. The product was recrystallized from ethyl acetate/hexane to provide 2S-{2R-[1S-hydroxycarbamoyl-2-(thiophen-2-ylsulphanyl)-ethyl]-4-methyl-pentanoylamino}-3-phenyl-propionic acid isopropyl ester as a white solid (707 mg, 65%). $^1$H-NMR; δ(methanol-d$_4$), 7.29 (1H, dd, J=1.5, 5.0 Hz), 7.13 (5H, m), 6.89–6.83 (2H, m), 4.88 (1H, m), 4.61 (1H, dd, J=4.6, 11.0 Hz), 3.12 (1H, dd, J=4.6, 13.9 Hz), 2.74 (1H, dd, J=11.1, 13.9 Hz), 2.33 (2H, m), 2.13 (1H, m), 1.90 (1H, dd, J=3.3, 13.2 Hz), 1.42–1.33 (2H, m), 1.14 (3H, d, J=6.3 Hz), 1.10 (3H, d, J=6.2 Hz), 0.90 (1H, m), 0.78 (3H, d, J=6.4 Hz) and 0.72 (3H, d, J=6.5 Hz). $^{13}$C-NMR; δ(methanol-d4), 175.4, 172.3, 171.0, 138.2, 134.3, 130.1, 129.6, 128.5, 128.2, 70.3, 55.2, 47.9, 47.8, 41.6, 39.0, 38.2, 26.4, 24.4, 21.9 and 21.6.

EXAMPLE 18

2S-[2-R-(1S-Hydroxycarbamoyl-ethyl)-4-methyl-pentanoylamino]-3,3-dimethyl-butyric acid 2-methoxy-ethyl ester

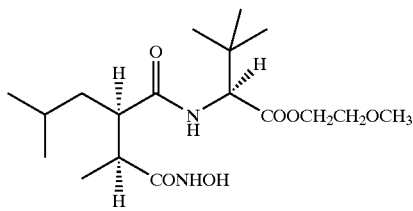

The title compound was prepared using an analogous route to that described for example 14 replacing L-phenylalanine with L-tert-leucine. $^1$H-NMR; δ(methanol-d$_4$), 4.26 (1H, s), 4.14 (2H, m), 3.50 (2H, m), 3.24 (3H, s), 2.60 (1H, dt, J=10.8, 3.2 Hz), 2.15 (1H, m), 1.49–1.19 (3H, m), 0.98 (3H, s), 0.95 (9H, s), 0.81 (3H, d, J=6.4 Hz) and 0.73 (3H, dd, J=6.5 Hz). $^{13}$C-NMR; δ(methanol-d$_4$), 176.9, 174.4, 172.2, 71.4, 64.6, 62.5, 58.9, 48.4, 42.1, 42.0, 34.8, 27.3, 26.9, 24.5, 21.8 and 17.0.

EXAMPLE 19

2S-(3S-Hydroxycarbamoyl-2R-isobutyl-hex-5-enoylamino)-3,3-dimethyl-butyric acid 2-methoxy-ethyl ester

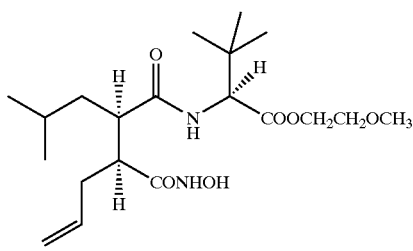

The title compound was prepared using an analogous route to that described for example 13 replacing L-phenylalanine with L-tert-leucine. $^1$H-NMR; δ(methanol-d$_4$), 8.28 (1H, d, J=8.6 Hz), 5.54 (1H, m), 4.88 (2H, m), 4.26 (1H, m), 4.14 (2H, m), 4.07 (2H, m), 3.24 (3H, s), 2.62 (1H, m), 2.17–1.95 (3H, bm), 1.44–1.18 (3H, bm), 1.00 (1H, m), 0.95 (9H, s), 0.81 (3H, d, J=6.4 Hz) and 0.73 (3H, d, J=6.5 Hz). $^{13}$C-NMR; δ(methanol-d$_4$), 176.8, 172.4, 172.1, 136.0, 117.5, 71.3, 64.6, 62.7, 62.6, 58.9, 48.3, 47.6, 41.8, 36.3, 35.1, 34.8, 30.7, 27.3, 26.8, 24.5 and 21.8.

EXAMPLE 20

2S-(3S-Hydroxycarbamoyl-2R-isobutyl-hex-5-enoylamino)-3-phenylpropionic acid cyclopentyl ester

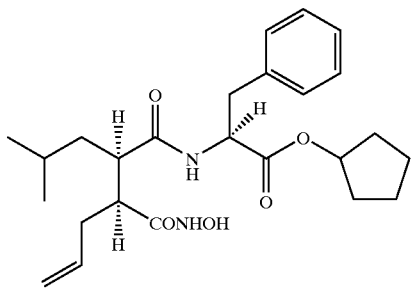

The title compound was prepared using an analogous route to that described for example 3 replacing L-phenylalanine isopropylester with L-phenylalanine cyclopentylester. $^1$H-NMR; δ(methanol-$d_4$), 7.18–7.02 (5H, m), 5.32 (1H, m), 5.06 (1H, m), 4.79–4.63 (3H, m), 3.10 (1H, dd, J=14.0, 5.1 Hz), 2.78 (1H, dd, J=13.9, 10.6 Hz), 2.36 (1H, dt, J=11.1, 3.0 Hz), 1.90 (1H, dt, J=11.6, 3.4 Hz), 1.80–1.16 (13H, bm), 0.89 (1H, m), 0.79 (3H, d, J=6.4 Hz) and 0.73 (3H, d, J=6.5 Hz). $^{13}$C-NMR; δ(methanol-$d_4$), 176.3, 172.7, 172.4, 138.3, 136.1, 130.2, 129.5, 128.0, 117.3, 79.6, 55.2, 47.9, 47.8, 41.6, 38.3, 35.7, 33.5, 26.6, 24.7, 24.5 and 21.7.

EXAMPLE 21

2S-(3S-Hydroxycarbamoyl-2R-isobutyl-hexanoylamino)-3-phenylpropionic acid isopropyl ester

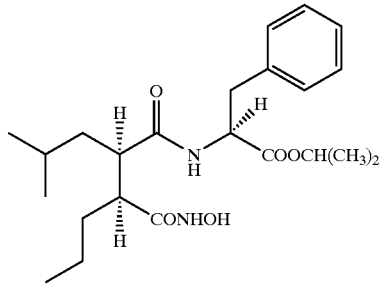

The title compound was prepared by an analogous route to that described for example 15. $^1$H-NMR; δ(methanol-$d_4$), 7.18–7.06 (5H, m), 4.90 (1H, sept, J=6.3 Hz), 4.64 (1H, dd, J=4.8, 10.7 Hz), 3.10 (1H, J=4.8, 14.0 Hz), 2.79 (1H, dd, J=10.6, 14.0 Hz), 2.35 (1H, dt, J=3.3, 11.2 Hz), 1.89 (1H, dt, J=3.3, 11.0 Hz), 1.39 (2H, m), 1.15 (3H, d, J=6.3 Hz), 1.09 (3H, d, J=6.3 Hz), 1.06–0.83 (4H, m), 0.80 (3H, d, J=6.5 Hz), 0.73 (3H, d, J=6.6 Hz), 0.58 (3H, t, J=7.2 Hz) and 0.50 (1H, m). $^{13}$C-NMR; δ(methanol-$d_4$), 176.6, 173.2, 172.5, 138.5, 130.2, 129.5, 127.9, 70.2, 55.3, 48.1, 47.4, 41.7, 38.3, 33.2, 26.5, 24.6, 22.0, 21.9, 21.7, 21.2 and 14.0.

EXAMPLE 22

2S-(3S-Hydroxycarbamoyl-2R-isobutyl-hex-5-enoylamino)-3,3-dimethyl-butyric acid isopropyl ester

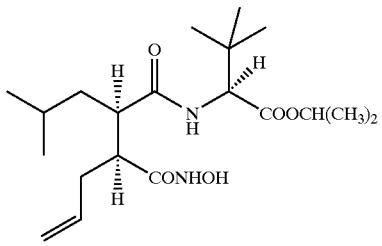

The title compound was prepared using an analogous route to that described for example 3 replacing L-phenylalanine with L-tert-leucine. $^1$H-NMR; δ(methanol-$d_4$), 5.56 (1H, m), 4.89 (3H, m), 4.20 (1H, m), 2.60 (1H, m), 2.21–1.93 (3H, bm), 1.50–1.24 (2H, m), 1.15 (6H, d, J=6.3 Hz), 1.00 (1H, m), 0.94 (9H, s), 0.82 (3H, d, J=6.5 Hz) and 0.73 (3H, d, J=6.5 Hz). $^{13}$C-NMR; δ(methano-$d_4$), 176.7, 172.4, 171.7, 136.0, 117.5, 69.9, 62.7, 48.1, 47.6, 41.8, 36.3, 34.7, 27.3, 26.8, 24.5, 22.0 and 21.9.

EXAMPLE 23

2R-(3S-Hydroxycarbamoyl-2R-isobutyl-hex-5-enoylamino)-3-phenylpropionic acid isopropyl ester

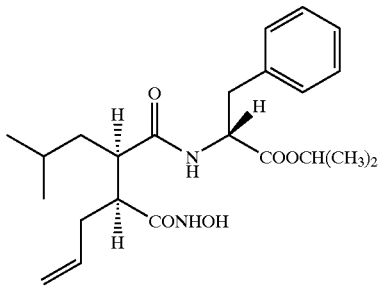

The title compound was prepared using an analogous route to that described for example 3 replacing L-phenylalanine isopropylester with D-phenylalanine isopropylester. $^1$H-NMR; δ(methanol-$d_4$), 7.11 (5H, m), 5.52 (1H, m), 4.89 (3H, m), 4.66 (1H, dd, J=11.0, 4.6 Hz), 3.15 (1H, dd, J=14.1, 4.6 Hz), 2.75 (1H, dd, J=14.1, 11.1 Hz), 2.34 (1H, m), 2.16 (2H, m), 2.08 (1H, m), 1.27 (1H, m), 1.15 (3H, d), J=14.0, 6.3 Hz), 1.10 (3H, d, J=6.3 Hz), 0.69 (2H, m) and 0.52 (6H, d, J=5.0 Hz). $^{13}$C-NMR; δ(methanol-$d_4$), 176.6, 172.5, 172.4, 138.4, 136.3, 130.1, 129.5, 127.8, 117.4, 70.3, 55.2, 48.4, 47.8, 41.0, 38.2, 36.1, 26.3, 24.4, 22.0 and 21.6.

EXAMPLE 24

2S-[2R-(S-Hydroxycarbamoyl-methoxy-methyl)-4-methyl-pentanoylamino]-3,3-dimethyl-butyric acid isopropyl ester

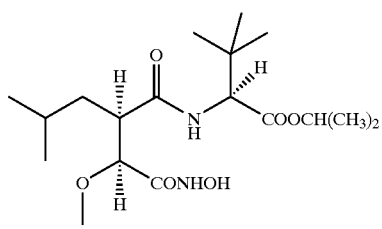

The title compound was prepared using an analogous route to that described for example 16 replacing L-phenylalanine with L-tert-leucine. $^1$H-NMR; δ(methanol-d$_4$), 4.92 (1H, m), 4.25 (1H, m), 3.42 (1H, d, J=9.8 Hz), 3.13 (3H, s), 2.77 (1H, m), 1.50–1.24 (2H, m), 1.15 (6H, d, J=6.3 Hz), 0.92 (9H, s), 0.87 (1H, m), 0.81 (3H, d, J=6.5 Hz), and 0.76 (3H, d, J=6.6 Hz). $^{13}$C-NMR; δ(methanol-d$_4$), 175.3, 171.7, 169.5, 82.9, 69.8, 62.3, 62.2, 58.0, 48.7, 38.3, 35.3, 27.1, 26.9, 24.2, 22.0 and 21.9.

EXAMPLE 25

2S-{(3S-Hydroxycarbamoyl-2R-isobutyl-hex-5-enoyl}-methyl-amino)-3-phenylpropionic acid isopropyl ester

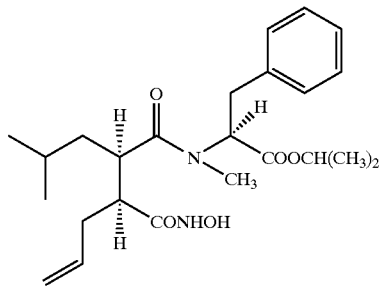

The title compound was prepared using an analogous route to that described for example 3 using N-methyl-L-phenylalanine isopropyl ester in place of L-phenylalanine isopropyl ester. $^1$H-NMR, δ(methanol-d$_4$), 7.18–7.00 (5H, m), 5.45 (1H, dd, J=11.8, 4.7 Hz), 5.34–5.17 (1H, m), 5.01–5.91 (1H, m), 4.85–4.66 (2H, m), 3.30 (1H, dd, J=14.6, 4.6 Hz), 3.02–2.84 (4H, m+s), 1.96–1.86 (1H, m), 1.68–1.50 (1H, m), 1.49–1.34 (2H, m), 1.16 (3H, d, J=6.2 Hz), 1.15 (3H, d, J=6.3 Hz), 1.01–1.10 (2H, m), 0.76 (3H, d, J=6.4, 6.5 Hz), 0.74 (3H, d, J=6.5 Hz). $^{13}$C-NMR; δ(methanol-d$_4$), 177.6, 172.4, 171.2, 128.2, 136.1, 130.1, 129.5, 128.1, 117.4, 70.4, 60.0, 42.8, 42.3, 35.3, 34.8, 33.8, 26.4, 24.5, 22.5, 22.0.

EXAMPLE 26

2S-(3S-Hydroxycarbamoyl-2R-isobutyl-hex-5-enoylamino)-3-phenylpropionic acid benzyl ester

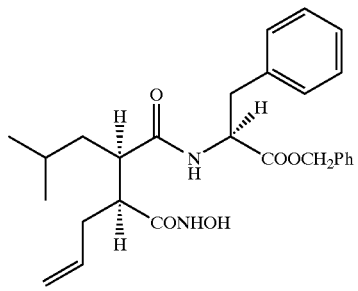

The title compound was prepared using an analogous route to that described for example 3 using L-phenylalanine benzyl ester in place of L-phenylalanine isopropyl ester. $^1$H-NMR; δ(methanol-d$_4$), 7.39–7.19 (10H, m), 5.55 (1H, m), 5.20 (2H, s), 4.89 (3H, m), 3.28 (1H, m), 2.95 (1H, dd, J=13.8, 10.8 Hz), 2.48 (1H, m), 2.03 (1H, dt, J=11.3, 3.2 Hz), 1.88 (1H, m), 1.45 (3H, m) 0.98 (1H, m), 0.81 (3H, d, J=6.4 Hz), 0.76 (3H, d, J=6.5 Hz). $^{13}$C-NMR; δ(methanol-d$_4$), 176.4, 172.7, 172.4, 138.3, 136.1, 129.6, 128.0, 117.3, 68.1, 55.2, 47.9, 41.6, 38.4, 35.7, 26.6, 24.5 and 21.6.

EXAMPLE 27

2S-(3S-Hydroxycarbamoyl-2R-isobutyl-hex-5-enoylamino)-4-methyl-pentanoic acid cyclopentyl ester

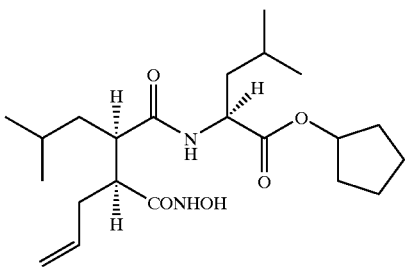

The title compound was prepared using an analogous route to that described for example 3 using L-leucine cyclopentyl ester in place of L-phenylalanine isopropyl ester. $^1$H-NMR; δ(DMSO-d$_6$), 10.52 (1H, d, J=1.5 Hz), 8.82 (1H, d, J=5.1 Hz), 8.42 (1H, d, J=7.4 Hz), 5.67–5.51 (1H, m), 5.08–5.01 (1H, m), 4.96–4.87 (2H, m), 4.28–4.19 (1H, m), 2.57–2.45 (1H, m), 2.27–2.04 (2H, m), 1.98–1.35 (14H, m), and 0.96–0.75 (13H, m). $^{13}$C-NMR; δ(DMSO-d$_6$), 174.3, 172.9, 170.0, 136.6, 117.1, 77.7, 51.2, 46.6, 40.2, 35.7, 32.9, 32.8, 25.8, 25.2, 25.1, 24.2, 23.8, 22.2 and 21.7.

EXAMPLE 28

3-Cyclohexyl-2S-(3S-hydroxycarbamoyl-2R-isobutyl-hex-5-enoylamino)-propionic acid cyclopentyl ester

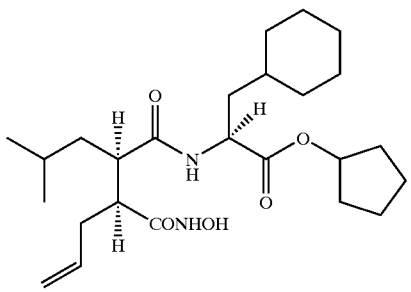

The title compound was prepared using an analogous route to that described for example 3 using L-cyclohexylalanine cyclopentyl ester in place of L-phenylalanine isopropyl ester. $^1$H-NMR; $\delta$(DMSO-d$_6$), 10.50 (1H, d, J=1.4 Hz), 8.79 (1H, d, J=1.6 Hz), 8.39 (1H, d, J=7.7 Hz), 5.71–5.54 (1H, m), 5.11–5.03 (1H, m), 4.99–4.89 (2H, m), 4.37–4.26 (1H, m), 2.61–2.49 (1H, m), 2.03–2.08 (2H, m), 2.02–0.74 (25H, m), 0.87 (3H, d, J=6.4 Hz) and 0.81 (3H, d, J=6.4 Hz). $^{13}$C-NMR; $\delta$(DMSO-d$_6$), 173.5, 172.3, 169.3, 135.9, 116.3, 77.0, 49.5, 46.0, 45.9, 40.3, 37.9, 35.0, 33.6, 33.2, 32.1, 31.2, 26.2, 26.1, 25.8, 25.2, 24.4, 23.5 and 21.5.

EXAMPLE 29

2S-(3S-Hydroxycarbamoyl-2R-isobutyl-hex-5-enoylamino)-3-phenylpropionic acid 1-methyl-piperidin-4-yl ester

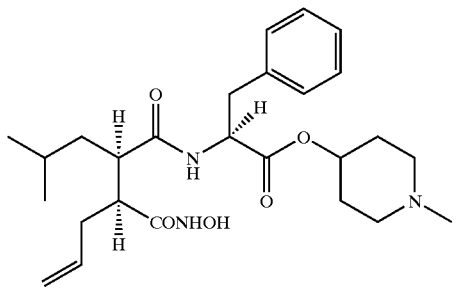

2S-(3S-Hydroxycarbamoyl-2R-isobutyl-hex-5-enoylamino)-3-phenylpropionic acid 1-ethyl-propyl ester.

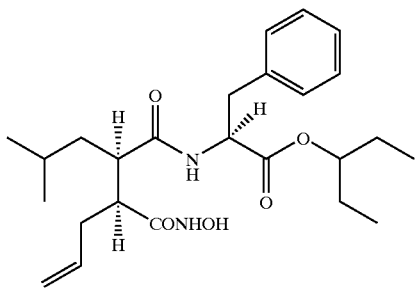

The title compound was prepared using an analogous route to that described for example 3 using L-phenylalanine 1-ethyl-propyl ester in place of L-phenylalanine isopropyl ester. $^1$H-NMR; $\delta$(methanol-d$_4$), 8.65 (1H, d, J=8.5 Hz), 7.31–7.711 (5H, m), 5.50–5.33 (1H, m), 4.88–4.74 (4H, m), 3.27 (1H, dd, J=9.7, 4.6 Hz), 2.88 (1H, dd, J=13.9, 11.0 Hz), 2.46 (1H, dt, J=11.1, 3.1 Hz), 1.99 (1H, dt, J=11.4, 3.4 Hz), 1.89–1.76 (1H, m), 1.70–1.49 (6H, m), 1.33–1.24 (1H, m), 1.07–0.94 (1H, m) and 0.94–0.60 (12H, m). $^{13}$C-NMR; $\delta$(methanol-d$_4$), 175.3, 172.0, 171.4, 137.4, 135.1, 129.2, 128.5, 127.0, 116.2, 78.5, 54.3, 46.9, 40.6, 37.5, 34.7, 26.7, 25.6, 23.5 and 20.7.

EXAMPLE 31

2S-(3S-Hydroxycarbamoyl-2R-isobutyl-hex-5-enoylamino)-3-phenylpropionic acid 1S-methyl-butyl-ester

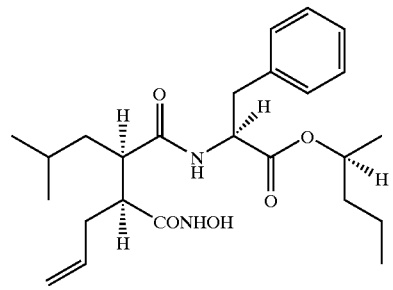

The title compound was prepared using an analogous route to that described for example 3 using L-phenylalanine 1S-methyl-butyl ester in place of L-phenylalanine isopropyl ester. $^1$H-NMR; $\delta$(methanol-d$_4$), 8.64 (1H, d, J=8.4 Hz), 7.29–7.12 (5H, m), 5.27 (1H, m), 4.89 (4H, m), 3.24 (1H, dd, J=13.9, 4.9 Hz), 2.88 (1H, dd, J=13.9, 10.8 Hz, 2.46 (1H, dt, J=11.3, 3.2 Hz), 1.99 (1H, dd, J=11.3, 3.4 Hz), 1.83 (1H, m), 1.64–1.41 (4H, bm), (3H, m), 1.23 (3H, d, J=6.3 Hz), 1.09 (1H, m), 0.90 (6H, m) and 0.83 (3H, d, J=6.5 Hz). $^{13}$C-NMR; $\delta$(methanol-d$_4$), 176.3, 172.6, 172.4, 138.4, 136.1, 130.3, 129.5, 128.0, 117.3, 73.3, 55.2, 47.9, 41.6, 39.1, 38.4, 35.7, 26.6, 24.6, 21.7, 20.3, 19.7 and 14.2.

EXAMPLE 32

2S-(3S-Hydroxycarbamoyl-2R-isobutyl-hex-5-enoylamino)-3-phenylpropionic acid cyclohexyl ester

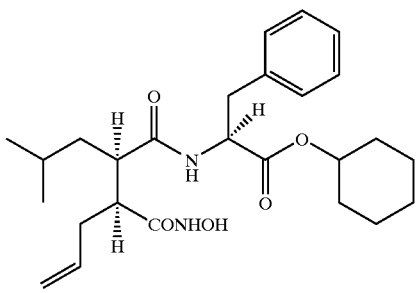

The title compound was prepared using an analogous route to that described for example 3 using L-phenylalanine cyclohexyl ester in place of L-phenylalanine isopropyl ester. $^1$H-NMR; $\delta$(DMSO-d$_6$), 10.39 (1H, s), 8.71 (1H, s), 8.42 (1H, d, J=8.0 Hz), 7.29–7.11 (5H, m), 5.39 (1H, ddt, J=17.0, 10.3, 6.6 Hz), 4.81 (1H, dd, J=10.3, 2.0 Hz), 4.73 (1H, dd, J=17.2, 2.0 Hz), 4.69–4.53 (2H, m), 3.09 (1H, dd, J=13.8, 4.8 Hz), 2.85 (1H, dd, J=13.8, 10.6 Hz), 2.47–2.34 (1H, m), 2.00–1.16 (15H, m), 0.93–0.78 (1H, m), 0.82 (3H, d, J=6.4 Hz) and 0.76 (3H, d, J=6.4 Hz). $^{13}$C-NMR; δ(DMSO-d$_6$), 173.7, 171.2, 169.6, 137.7, 136.2, 129.4, 128.4, 126.8, 116.2, 73.0, 53.7, 46.2, 45.9, 40.5, 36.9, 34.7, 31.3, 31.2, 25.3, 25.2, 24.6, 23.5 and 21.8.

EXAMPLE 33

2S-{2R-[1S-Hydroxycarbamoyl-2-(thiophen-2-ylsulphanyl)-ethyl]-4-methyl-pentanoylamino}-3,3-dimethyl-butyric acid isopropyl ester

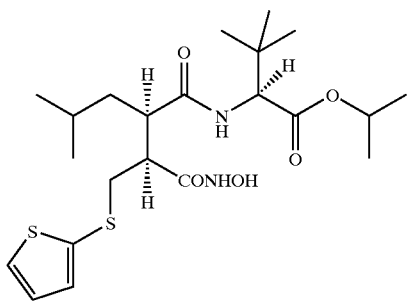

The title compound was prepared using an analogous route to that described for example 17. 2-[1R-(1S-Isopropoxycarbonyl-2,2-dimethyl-propylcarbamoyl)-3-methyl-butyl]-acrylic acid was prepared from 3R-hydroxycarbonyl-2-benzyloxycarbonyl-5-methylhexanoic acid benzyl ester and L-tert-butyl glycine isopropyl ester using methods similar to those described in example 4. $^1$H-NMR; δ(methanol-d$_4$), 7.44 (1H, m), 7.11 (1H, m), 6.96 (1H, m), 4.98 (1H, m), 4.23 (1H, s), 3.00 (1H, m), 2.79 (2H, m), 2.42 (1H, m), 1.53 (1H, m), 1.37 (1H, m), 1.24 (3H, s), 1.21 (3H, s), 1.11 (1H, m), 1.00 (9H, s), 0.88 (3H, d, J=6.4 Hz) and 0.81 (3H, d, J=6.6 Hz). $^{13}$C-NMR; δ(methanol-d$_4$), 176.3, 172.0, 171.5, 135.3, 131.2, 129.1, 70.3, 63.0, 48.4, 48.1, 42.0, 40.8, 35.2, 27.8, 27.2, 24.8, 22.5 and 22.2.

EXAMPLE 34

2S-(3S-Hydroxycarbamoyl-2R-isobutyl-hex-5-enoylamino)-3-phenylpropionic acid 1R-methyl-butyl ester

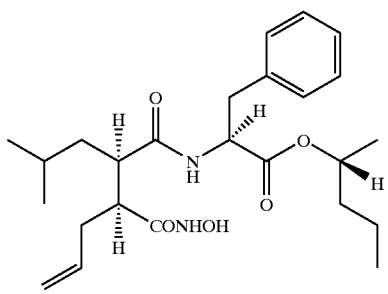

The title compound was prepared using an analogous route to that described for example 3 using L-phenylalanine 1R-methyl-butyl ester in place of L-phenylalanine isopropyl ester. $^1$H-NMR; δ(methanol-d$_4$), 7.30–7.12 (5H, m), 5.57–5.34 (1H, m), 5.01–4.93 (1H, m), 4.84–4.70 (3H, m), 3.22 (1H, dd, J=13.9, 14.9 Hz), 2.88 (1H, dd, J=13.9, 10.9 Hz), 2.46 (1H, dt, J=11.1, 3.0 Hz), 1.99 (1H, dt, J=11.4, 3.3 Hz), 1.90–1.77 (1H, m), 1.68–1.21 (7H, m), 1.16 (3H, d, J=6.3 Hz), 1.12–0.89 (7H, m), and 0.38 (3H, d, J=6.5 Hz). $^{13}$C-NMR; δ(methanol-d$_4$), 176.3, 172.6, 172.4, 138.3, 137.9, 136.1, 130.3, 129.5, 128.0, 117.3, 73.2, 55.4, 47.9, 41.6, 39.2, 38.4, 35.7, 26.6, 24.6, 21.7, 20.2, 19.7 and 14.2.

EXAMPLE 35

2S-(3S-Hydroxycarbamoyl-2R-isobutyl-hex-5-enoylamino)-3-phenylpropionic acid tetrahydro-furan-3(R, S)-yl ester

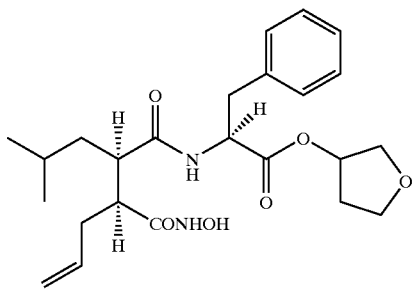

The title compound was prepared using an analogous route to that described for example 3 using L-phenylalanine tetrahydro-furan-3(R, S)-yl ester in place of L-phenylalanine isopropyl ester. $^1$H-NMR; δ(methanol-d$_4$), 7.29–7.13 (5H, m), 5.51–5.29 (2H, m), 4.85–4.75 (3H, m), 3.91–3.66 (4H, m), 3.23 (1H, dd, J=14.0, 5.0 Hz), 2.96–2.86 (1H, m), 2.47 (1H, dt, J=11.0, 3.0 Hz), 2.28–2.10 (1H, m), 2.05–1.78 (3H, m), 1.55–1.44 (2H, m), 1.37–1.30 (1H, m), 1.03–0.92 (1H, m), 0.89 (3H, d, J=6.4 Hz) and 0.83 (3H, d, J=6.5 Hz). $^{13}$C-NMR, δ(methanol-d$_4$), 176.5, 172.7, 172.4, 138.2, 136.1, 130.3, 129.6, 128.1, 117.3, 77.3, 73.8, 67.9, 55.2, 47.9, 41.6, 38.2, 33.2, 26.7, 24.5 and 21.7.

EXAMPLE 36

2S-(3S-Hydroxycarbamoyl-2R-isobutyl-hex-5-enoylamino)-3,3-dimethyl-butyric acid cyclopentyl ester

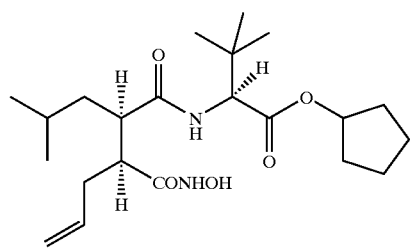

The title compound was prepared using an analogous route to that described for example 3 using L-tert-butyl glycine cyclopentyl ester in place of L-phenylalanine isopropyl ester. $^1$H-NMR; δ(methanol-d$_4$), 5.71–5.57 (1H, m), 5.18–5.13 (1H, m), 5.03–4.95 (2H, m), 4.29 (1H, s), 2.76–2.66 (1H, m), 2.31–2.03 (3H, m), 1.90–1.38 (10H, m), 1.14–0.99 (2H, m), 1.06 (9H, s), 0.92 (3H, d, J=6.5 Hz) and 0.87 (3H, d, J=6.5 Hz). $^{13}$C-NMR; δ(methanol-d$_4$), 177.2, 172.8, 172.5, 136.4, 117.9, 79.7, 63.1, 42.2, 36.8, 35.2, 34.0, 33.8, 27.7, 25.1, 25.0, 24.9 and 22.3.

EXAMPLE 37

2S-[2R-(1S-Cyclopentyl-hydroxycarbamoyl-methyl)-4-methyl-pentanoylamino]-3-phenyl-propionic acid cyclopentyl ester

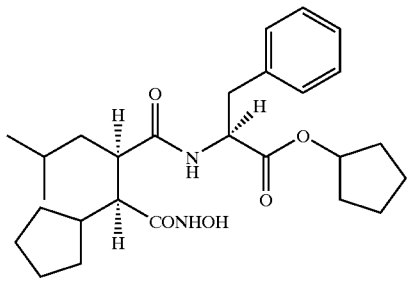

The title compound was prepared using chemistry analogous to that described in WO 97/19053 involving an initial coupling between 2S-cyclopentyl-3R-isobutyl-succinic acid 1-benzyl ester and L-phenylalanine cyclopentyl ester. $^1$H-NMR; δ(methanol-d$_4$), 8.51 (1H, d, J=8.1 Hz), 7.31–7.16 (5H, m), 5.13–5.04 (1H, m), 4.73–4.62 (3H, m), 3.01 (1H, dd, J=13.9, 6.4 Hz), 2.92 (1H, dd, J=13.9, 8.8 Hz), 2.78 (1H, dt, J=10.7, 3.8 Hz), 2.24–2.02 (3H, m), 1.90–1.21 (20H, m), 1.12–0.96 (1H, m), and 0.93–0.81 (1H, m). $^{13}$C-NMR; δ(methanol-d$_4$), 176.5, 173.2, 172.9, 144.0, 138.5, 130.6, 129.9, 128.4, 113.8, 79.8, 55.6, 51.5, 42.6, 41.3, 39.2, 33.9, 33.8, 32.3, 30.2, 26.5, 26.1, 25.0, 22.8 and 22.1.

EXAMPLE 38

2S-[2R-(1S-Hydroxy-hydroxycarbamoyl-methyl)-pent-4-ynoylamino]-3-phenylpropionic acid cyclopentyl ester

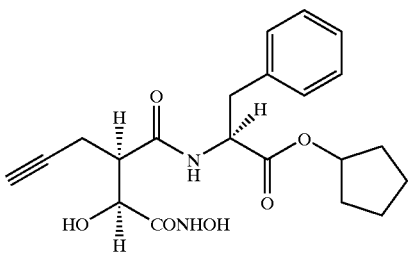

(a) 2S-Hydroxy-3R-prop-2-ynyl-succinic acid diisopropyl ester

A solution of S-malic acid diisopropyl ester (5.5 g, 25.2 mmol) in dry THF (20 ml) was added to a solution of freshly prepared lithium disopropylamide [from N,N-diisopropylamine (6.9 mL, 52. mmol) and 2.5 M n-butyllithium (21 mL, 52.5 mmol)] in dry THF (50 mL), whilst maintaining the temperature at −5° C. The reaction mixture was stirred at −5° C. for 75 minutes then cooled to −70° C. A solution of propargyl bromide (80% solution in toluene, 3.1 mL, 27.7 mmol) was added slowly, whilst maintaining the temperature at −70° C. The cooling bath was removed and the solution was stirred overnight before quenching with saturated aqueous ammonium chloride (50 mL). The aqueous layer was separated and extracted with ethyl acetate. The organic layers were combined and washed with 1M hydrochloric acid and brine and dried over anhydrous magnesium sulphate. The solution was filtered and concentrated in vacuo to give a brown oil which was purified by column chromatography (silica gel, 25% ethyl acetate in hexane) to provide the title compound as an orange oil (1.4 g, 22%; 9:1 mixture of diastereomers by NMR). $^1$H-NMR; δ(CDCl$_3$, major diastereoisomer), 5.12 (1H, m), 5.04 (1H, m), 4.45 (1H, dd, J=5.8, 2.6 Hz), 3.17 (1H, d, J=5.8 Hz), 3.08 (1H, m), 2.67 (1H, m), 2.05 (1H, t, J=2.9 Hz), 1.29 (6H, d, J=6.1 Hz) and 1.19 (6H, d, J=6.2 Hz).

(b) 2S-Hydroxy-3R-prop-2-ynyl-succinic acid

A solution of 2S-hydroxy-3R-prop-2-ynyl-succinic acid diisopropyl ester (2.47 g, 9.5 mmol) in 1M solution hydroxide (32 mL, 3 mmol) was heated at reflux for 1 hour then cooled to room temperature. The solution was acidified to pH 2 with 1M hydrochloric acid and extracted with ethyl acetate. The combined organics were dried over magnesium sulphate, filtered and concentrated in vacuo to provide the title compound as a brown oil (0.94 g, 64%). $^1$H-NMR; δ(methanol-d$_4$), 4.37 (1H, d, J=3.4 Hz), 3.01 (1H, m), 2.51 (2H, m), 2.21 (1H, t, J=2.5 Hz).

(c) 2R-(2,2-Dimethyl-5-oxo-[1,3]dioxolan-4S-yl)-pent-4-ynoic acid 2S-Hydroxy-3R-prop-2-ynyl-succinic acid (0.94 g, 6.18 mmol) was dissolved in ethyl acetate (5 mL). Dimethoxypropane (10 mL) and p-toluenesulfonic acid (10 mg) were added and the solution heated at reflux for 2.5 hours. Solvents were removed in vacuo to provide the title compound as a dark brown gum (1.0 g, 84%). $^1$H-NMR; δ(CDCl$_3$), 4.80 (1H, d, J=2.4 Hz), 3.22 (1H, m), 2.86 (1H, ddd, J=17.2, 5.4, 2.6 Hz), 2.61 (1H, ddd, J=13.0, 10.3, 2.6 Hz), 2.10 (1H, t, J 2.8 Hz), 1.58 (3H, s) and 1.57 (3H, s).

(d) 2S-[2R-(1S-Hydroxy-hydroxycarbamoyl-methyl)-pent-4-ynoylamino]-3-phenylpropionic acid cyclopentyl ester The title compound was prepared using an analogous route to that described in example 8. 2R-(2,2-Dimethyl-5-oxo-[1,3]dioxolan-4S-yl)-pent-4-ynoic acid pentafluorophenyl ester was prepared by treatment of 2R-(2,2-dimethyl-5-oxo-[1,3]dioxolan-4S-yl)-pent-4-ynoic acid with pentafluorophenol and N-(3-dimethylaminopropyl)-N'-ethylcarbodiimide hydrochloride in DCM. $^1$H-NMR; δ(methanol-d$_4$), 7.31–7.18 (5H, m), 5.09–5.05 (1H, m), 4.64–4.58 (1H, m), 4.27 (1H, d, J=5.4 Hz), 3.06–2.92 (3H, m), 2.48 (2H, dd, J=7.6, 2.6 Hz), 2.32 (1H, t, J=2.6 Hz) and 1.84–1.47 (8H, bm). $^{13}$C-NMR; δ(methanol-d$_4$), 173.8, 172.6, 171.2, 137.8, 130.4, 129.5, 127.9, 79.7, 71.9, 55.4, 49.2, 38.8, 33.4, 33.3, 24.5 and 19.3.

EXAMPLE 39

2S-(3S-Hydroxycarbamoyl-2R-isobutyl-hex-5-enoylamino)-3-pyridin-3-yl-propionic acid cyclopentyl ester

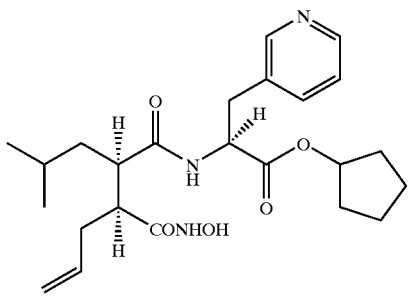

The title compound was prepared using an analogous route to that described for example 3 using L-3- pyridylalanine cyclopentyl ester in place of L-phenylalanine isopropyl ester. ¹H-NMR; δ(DMSO-d₆), 10.42 (1H, bs), 8.67 (1H, bs), 8.51–8.33 (3H, m), 7.74 (1H, d, J=7.9 Hz), 7.28 (1H, dd, J=7.7, 4.8 Hz), 5.37 (1H, ddt, J=17.0, 10.2, 6.7 Hz), 5.09–5.02 (1H, m), 4.82 (1H, dd, J=10.2, 2.0 Hz), 4.73 (1H, dd, J=17.2, 2.0 Hz), 4.68–4.56 (1H, m), 3.12 (1H, dd, J=14.1 4.8 Hz), 2.86 (1H, dd, J=14.0, 11.0 Hz), 2.41–2.30 (1H, m), 1.96–1.80 (13H, m), 0.92–0.74 (1H, m), 0.80 (3H, d, J=6.4 Hz) and 0.76 (3H, d, J=6.5 Hz). ¹³C-NMR; δ(methanol-d₄), 173.7, 171.3, 169.5, 150.5, 147.9, 137.2, 133.4, 123.6, 116.4, 77.6, 53.0, 46.2, 45.9, 34.6, 33.9, 32.4, 32.3, 25.3, 24.6, 23.7 and 2.17.

EXAMPLE 40

3-tert-Butoxy-2S-(3S-hydroxycarbamoyl-2R-isobutyl-hex-5-enoylamino)-propionic acid cyclopentyl ester

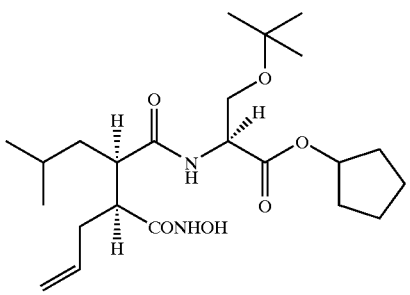

The title compound was prepared using an analogous route to that described for example 3 using L-tert-butoxyserine cyclopentyl ester in place of L-phenylalanine isopropyl ester. ¹H-NMR; δ(CDCl₃), 6.66 (1H, d, J=8.1 Hz), 5.73–5.63 (1H, m), 5.27–5.22 (1H, m), 5.10–4.99 (2H, m), 4.72–4.67 (1H, m), 3.80 (1H, dd, J=8.8, 3.0 Hz), 3.57 (1H, dd, J=8.8, 3.0 Hz), 2.65–2.57 (1H, m), 2.53–2.34 (2H, m), 2.22–2.17 (1H, m), 1.88–1.56 (11H, m), 1.19 (9H, s), 0.91 (3H, d, J=6.5 Hz) and 0.87 (3H, d, J=6.5 Hz). 46.2, 39.7, 34.7, 32.6, 32.4, 27.2, 25.8, 23.8, 23.7, 23.6 and 21.3.

EXAMPLE 41

2S-(3-Hydroxycarbamoyl-2R-isobutyl-hex-5-enoylamino)-2-phenylethanoic acid cyclopentyl ester

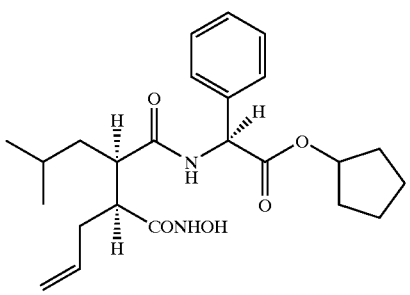

The title compound was prepared using an analogous route to that described for example 3 using L-phenylglycine cyclopentyl ester in place of L-phenylalanine isopropyl ester. ¹H-NMR; δ(methanol-d₄), 7.41–7.32 (5H, m), 5.70–5.49 (1H, m), 5.42 (1H, s), 5.21–5.15 (1H, m), 4.92–4.85 (2H, m), 2.69–2.61 (1H, m), 2.20–2.13 (2H, m), 1.95–1.51 (11H, m), 1.18–1.00 (1H, m), 0.95 (3H, d, J=6.5 Hz) and 0.89 (3H, d, J=6.5 Hz). ¹³C-NMR; δ(methanol-d₄), 176.3, 172.3, 171.5, 137.5, 135.9, 129.8, 129.6, 129.0, 117.4, 79.8, 58.7, 58.6, 48.3, 47.3, 41.5, 36.0, 33.3, 26.7, 24.5, 24.4 and 21.7.

EXAMPLE 42

2S-[5-(2-Chlorophenyl)-2R-(1S-hydroxy-hydroxycarbamoyl-methyl)-pent-4-ynoylamino]-3-phenylpropionic acid cyclopentyl ester

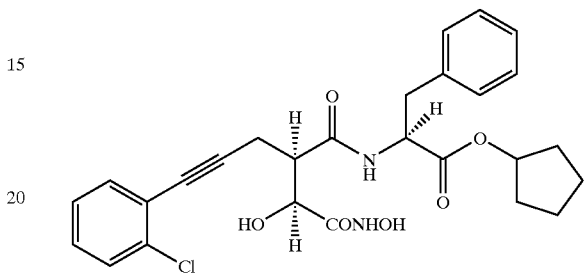

(a) 5-(2-Chlorophenyl)-2R-(2,2-dimethyl)-5-oxo-[1,3]-dioxolan-4S-yl)-pent-4-ynoic acid 2R-(2,2-Dimethyl-5-oxo-[1,3]-dioxolan-4S-yl)-pent-4-ynoic acid (example 38, 3 g, 15.6 mmol) and 1-chloro-2-iodobenzene (1.59 mL, 13.0 mmol) were dissolved in a mixture of diisopropylamine (5.2 mL) and DCM (20 mL) in a 35 mL pressure tube. Dichlorobis(triphenylphosphine)palladium(II) (379 mg, 4.6 mol %) and copper (I) iodide (89 mg, 4.0 mol %) were added and the tube heated at room temperature for 4 hours. The reaction mixture was partitioned between DCM and 1M hydrochloric acid. The product was extracted with saturated aqueous sodium hydrogen carbonate. The basic extracts were combined, acidified to pH2 with 1M hydrochloric acid then extracted with dichloromethane. Combined organics were dried (magnesium sulphate), filtered and solvents removed in vacuo to provide the title compound as an orange solid (3.2 g, 81%). ¹H-NMR; δ(CDCl₃), 7.46–7.37 (2H, m), 7.28–7.17 (2H, m), 5.00 (1H, d=2.8 Hz), 3.39–3.32 (1H, m), 3.16 (1H, dd, J=17.3, 5.2 Hz), 2.92 (1H, dd, J=17.8, 10.7 Hz), 1.60 (3H, s) and 1.58 (3H, s).

(b) 2S-[5-(2-Chlorophenyl)-2R-(1S-hydroxycarbamoyl-methyl)-pent-4-ynoylamino]-3-phenylpropionic acid cyclopentyl ester.

The title compound was prepared using an analogous route to that described for example 8 using 5-(2-chlorophenyl)-2R-(2,2-dimethyl)-5-oxo-[1,3]-dioxolan-4S-yl)-pent-4-ynoic acid pentafluorophenyl ester in place of 2R-(2,2-dimethyl-5-oxo-[1,3-dioxolan-4S-yl)-4-methyl-pentanoic acid pentafluorophenyl ester. The pentafluorophenyl ester was prepared by treatment of 5-(2-chlorophenyl)-2R-(2,2-dimethyl)-5-oxo-[1,3]-dioxolan-4S-yl)pent-4-ynoic acid with pentafluorophenol and N-(3-dimethylaminopropyl)-N'-ethylcarbodiimide hydrochloride in DCM. ¹H-NMR; δ (methanol-d₄), 8.30 (1H, d, J=6.8 Hz), 7.48–7.23 (9H, bm), 5.00 (1H, m), 4.67–4.65 (1H, m), 4.35 (1H, d, J=4.6 Hz), 3.10–2.97 (3H, m), 2.78 (2H, d, J=7.1 Hz) and 1.69–1.50 (8H, bm). ¹³C-NMR; δ (methanol-d₄), 173.8, 172.5, 171.3, 137.8, 136.8, 134.7, 130.5, 130.3, 130.2, 129.5, 127.9, 127.7, 92.9, 80.3, 79.6, 72.2, 55.5, 39.0, 33.5, 33.3, 24.6, 24.5 and 20.2.

EXAMPLE 43

2S-(3S-Hydroxycarbamoyl-2R-isobutyl-6-phenyl-hex-5-enoylamino)-3-phenyl-propionic acid cyclopentyl ester

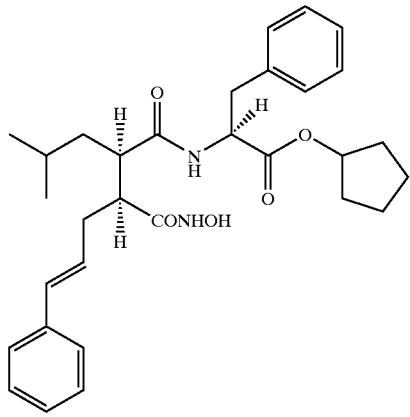

(a) 2S-[1R-(1S-Cyclopentyloxycarbonyl-2-phenyl-ethylcarbamoyl)-3-methyl-butyl]-5-phenyl-pent-4-enoic acid.

A solution of 2S-[1R-(1S-cyclopentyloxycarbonyl-2-phenyl-ethylcarbamoyl)-3-methyl-butyl]-pent-4-enoic acid. (previously prepared for example 20) (400 mg, 0.93 mmol), palladium acetate (10.5 mg, 0.05 mmol), tri-ortho-tolyl phosphine (28 mg, 0.1 mmol), iodobenzene (208 μL, 1.86 mmol) and triethylamine (250 μL, 1.86 mmol)) in acetonitrile was heated at 75° C. for 1 hour. The cooled reaction mixture was partitioned between ethyl acetate and 1.0M hydrochloric acid. The organic layer was washed with water and brine, dried over anhydrous magnesium sulphate, filtered and evaporated. Purification by chromatography on silica gel gave the product as a white powder (99 mg, 0.2 mmol, 21%). $^1$H-NMR; δ (CDCl$_3$), 7.36–7.18 (8H, m), 7.13–7.07 (2H, m), 6.37 (1H, d, J=15.7 Hz), 6.17 (1H, d, J=8.1 Hz), 6.08–5.96 (1H, m), 5.23–5.17 (1H, m), 4.91–4.80 (1H, m), 3.18 (1H, dd, J=14.0, 5.9 Hz), 3.01 (1H, dd, J=14.0, 7.0 Hz), 2.63–2.50 (2H, m), 2.45–2.37 (1H, m), 2.23–2.07 (1H, m), 1.92–1.44 (10H, m), 1.27–1.24 (1H, m), 0.86 (3H, d, J=6.5 Hz), 0.85 (3H, d, J=6.4 Hz).

(b) 2S-(3S-Hydroxycarbamoyl-2R-isobutyl-6-phenyl-hex-5-enoylamino)-3-phenyl-propionic acid cyclopentyl ester.

The title compound was prepared from 2S-[1R-(1S-cyclopentyloxycarbonyl-2-phenyl-ethylcarbamoyl)-3-methyl-butyl]-5-phenyl-pent-4-enoic acid using chemistry previously described eg example 3c. $^1$H-NMR; δ (methanol-d$_4$), 8.63–8.49 (1H, m), 7.24–6.96 (10H, m), 6.17–6.02 (1 h, m), 5.90–5.69 (1H, m), 5.13–5.04 (1H, m), 4.75–4.68 (1H, m), 3.13 (1H, dd, J=13.9, 5.4 Hz), 2.81 (1H, dd, J=13.9, 10.5 Hz), 2.53–2.29 (2H, m), 2.01–1.34 (12H, m), 1.02–0.90 (1H, m), 0.83 (3H, d, J=6.4 Hz), 0.75 (3H, d, J=6.6 Hz).

Biological Example

The compounds of examples 1–5 were tested in the following cell proliferation assay, to determine their respective capacities to inhibit proliferation of the cell types in question.

Two human cell lines namely a histiocytic lymphoma (U937) and a melanoma (RPMI-7951) were seeded into 30 mm$^2$ tissue culture wells, in the appropriate culture medium supplemented with 10% fetal calf serum at a density of 250 cells/mm$^2$. Six hours later the test compounds were added in the same culture medium to the cells to give a final concentration of 6 μM. Control wells contained cells supplemented with the same culture medium containing the equivalent amount of drug vehicle, which in this case was DMSO at a final concentration of 0.08%. After 72 hours in culture the cells were pulsed for 3 hours with [methyl-$^3$[H] Thymidine] (2 μCi/ml) and then harvested onto filter mats and DNA associated radioactivity counted. Results are expressed as percentage of control $^3$[H] Thymidine incorporation (n=6±1 stdv).

The results obtained are set out in the following Table:

| | Activities | |
|---|---|---|
| Example | U937 | RPMI |
| 1 | 7 | 40 |
| 2 | 7 | 37 |
| 3 | 2.5 | 27 |
| 4 | 93 | not tested |
| 5 | 19 | 82 |

Further examples were tested in the U937 assay described above at 6 μM and the results, expressed as percentage of control $^3$[H] Thymidine incorporation (n=6±1 stdv), are set out in the following Table:

| Example | U937 |
|---|---|
| 6 | 18 |
| 7 | 0 |
| 8 | 1 |
| 9 | 8 |
| 10 | 1 |
| 11 | 0 |
| 12 | 10 |
| 13 | 4 |
| 14 | 33 |
| 15 | 19 |
| 16 | 2 |
| 17 | 0 |
| 18 | 54 |
| 19 | Not tested |
| 20 | 0 |
| 21 | 1 |
| 22 | 51 |
| 23 | 36 |
| 24 | 50 |
| 25 | 34 |
| 26 | 0 |
| 27 | 0 |
| 28 | 0 |
| 29 | 49 |
| 30 | 6 |
| 31 | 7 |
| 32 | 0 |
| 33 | Not tested |
| 34 | 3 |
| 35 | 14 |
| 36 | 51 |
| 37 | 0 |
| 38 | 37 |
| 39 | 26 |
| 40 | 0 |
| 41 | 0 |
| 42 | 0 |
| 43 | Not tested |

For comparison, the activity in the above U937 assay of the known cytotoxic agent 5-fluorouracil (5-FU) at 6 μM was found to be 50% of that observed with the vehicle alone.

What is claimed is:

1. A compound formula (I)

$$\text{(I)}$$

[Structure: R_2 and R_1 substituents on a backbone with C(=O)-N(R)- linkage, R_3 and R_4 on adjacent carbon, with CONHOH group]

wherein
R is hydrogen or $(C_1-C_6)$alkyl;
$R_1$ is hydrogen;
$(C_2-C_6)$alkyl;
$(C_2-C_6)$alkenyl;
phenyl or substituted phenyl;
phenyl $(C_2-C_6)$alkyl or substituted phenyl $(C_2-C_6)$ alkyl;
phenyl $(C_2-C_6)$alkenyl or substituted phenyl$(C_2-C_6)$ alkenyl;
heterocyclyl or substituted heterocyclyl;
heterocyclyl$(C_2-C_6)$alkyl or substituted heterocyclyl $(C_2-C_6)$alkyl;
a group $BSO_nA$- wherein n is 0, 1 or 2 and B is hydrogen or a $(C_2-C_6)$alkyl, phenyl, substituted phenyl, heterocyclyl substituted heterocyclyl, $(C_2-C_6)$acyl, phenacyl or substituted phenacyl group, and A represents $(C_2-C_6)$alkylene;
hydroxy or $(C_2-C_6)$alkoxy;
amino, protected amino, acylamino, $(C_2-C_6)$ alkylamino or di-$(C_2-C_6)$alkylamino;
mercapto or $(C_2-C_6)$alkylthio;
amino$(C_2-C_6)$alkyl, $(C_2-C_6)$alkylamino$(C_2-C_6)$alkyl, di$(C_2-C_6)$alkylamino$(C_2-C_6)$alkyl, hydroxy$(C_2-C_6)$ alkyl, mercapto$(C_2-C_6)$alkyl or carboxy$(C_2-C_6)$ alkyl wherein the amino-, hydroxy-, mercapto- or carboxyl-group are optionally protected or the carboxyl- group amidated;
lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl or non-aromatic heterocyclic ring containing up to 3 heteroatoms, any of which may be (i) substituted by one or more substituents selected from $C_1-C_6$ alkyl, $C_2-C_6$ alkenyl, halo, cyano (—CN), —$CO_2H$, —$CO_2R$, —$CONH_2$, —CONHR, —$CON(R)_2$, —OH, —OR, oxo-, —SH, —NHCOR, and —$NHCO_2R$ wherein R is $C_2-C_6$ alkyl or benzyl and/or (ii) fused to a cycloalkyl or heterocyclic ring;
$R_2$ is a $C_1-C_{12}$ alkyl,
$C_2-C_{12}$ alkenyl,
$C_2-C_{12}$ alkynyl,
phenyl$(C_1-C_6$ alkyl)-,
heteroaryl$(C_1-C_6$ alkyl)-,
phenyl$(C_2-C_6$ alkenyl)-,
heteroaryl$(C_2-C_6$ alkynyl)-,
cycloalkyl$(C_1-C_6$ alkyl)-,
cycloalkyl$(C_2-C_6$ alkenyl)-,
cycloalkyl$(C_2-C_6$ alkynyl)-,
cycloalkenyl$(C_1-C_6$ alkyl)-,
cycloalkenyl$(C_2-C_6$ alkenyl)-,
cycloalkenyl$(C_2-C_6$ alkynyl)-,
phenyl$(C_1-C_6$ alkyl)O$(C_1-C_6$ alkyl)-, or
heteroaryl$(C_1-C_6$ alkyl)O$(C_1-C_6$ alkyl)- group,
any one of which may be substituted by
  $C_1-C_6$ alkyl,
  $C_1-C_6$ alkoxy,
  halo,
  cyano (—CN),
  phenyl, or
  phenyl substituted by
    $(C_1-C_6)$ alkyl,
    $(C_2-C_6)$ alkoxyl,
    halo, or
    cyano (—CN);
$R_3$ is the side chain of a natural or non-natural α amino acid in which any functional groups may be protected; and
$R_4$ is an ester or thioester group of the formula $R_9$O(C=O)— —(C=O)$SR_9$, —(C=S)$SR_9$, or —(C=S) $OR_9$ wherein $R_9$ is $(C_1-C_6)$alkyl, $(C_2-C_6)$alkenyl, cycloalkyl, cycloalkyl$(C_1-C_6)$alkyl-, phenyl, heterocyclyl, phenyl$(C_1-C_6)$alkyl-, heterocyclyl $(C_1-C_6)$alkoxy$(C_1-C_6)$alkoxy$(C_1-C_6)$alkoxy$(C_1-C_6)$ alkyl-, any of which may be substituted on a ring or non-ring carbon atom or on a ring heteroatom,
or a pharmaceutically acceptable salt, hydrate or solvate thereof,
PROVIDED THAT:
(i) (i) when R and $R_1$ are hydrogen, $R_2$ is 4-chlorophenylpropyl, and $R_3$ is tertbutyl, then $R_4$ is not a methyl carboxylate ester group; and
(ii) when R and $R_1$ are hydrogen, $R_2$ is phenylmethyl, and $R_3$ is 1-methylprop-1-yl, then $R_4$ is not a tert-butyl carboxylate ester group.

2. A compound as claimed in claim 1 wherein the stereochemical configuration of the carbon atom carrying the group $R_3$ and $R_4$ is S.

3. A compound as claimed in claim 1 wherein $R_4$ is n-propyl, allyl, methoxy or thienylsulfanyl-methyl.

4. A compound as claimed in claim 2 wherein $R_4$ is n-propyl, allyl, methoxy or thienylsulfanyl-methyl.

5. A compound as claimed in claim 1 wherein $R_2$ is:
$C_1-C_{12}$ alkyl, $C_3-C_6$ alkenyl or $C_3-C_6$ alkynyl;
phenyl$(C_1-C_6$ alkyl)-, phenyl$(C_3-C_6$ alkenyl)- or phenyl $(C_3-C_6$ alkynyl)- optionally substituted in the phenyl ring;
heteroaryl$(C_1-C_6$ alkyl)-, heteroaryl $(C_3-C_6$ alkenyl)- or heteroaryl $(C_3-C_6$ alkynyl)- optionally substituted in the heteroaryl ring.

6. A compound as claimed in claim 2 wherein $R_2$ is:
$C_1-C_{12}$ alkyl, $C_3-C_6$ alkenyl or $C_3-C_6$ alkynyl;
phenyl$(C_1-C_6$ alkyl)-, phenyl$(C_3-C_6$ alkenyl)- or phenyl $(C_3-C_6$ alkynyl)- optionally substituted in the phenyl ring;
heteroaryl$(C_1-C_6$ alkyl)-, heteroaryl $(C_3-C_6$ alkenyl)- or heteroaryl $(C_3-C_6$ alkynyl)- optionally substituted in the heteroaryl ring.

7. A compound as claimed in claim 1 wherein $R_2$ is isobutyl, n-hexyl, or 3-(2-chlorophenyl)prop-2-yn-1-yl.

8. A compound as claimed in claim 2 wherein $R_2$ is isobutyll n-hexyl, or 3-(2-chlorophenyl)prop-2-yn-1-yl.

9. A compound as claimed in claim 1 wherein $R_3$ is $C_1-C_6$ alkyl, phenyl, 2, -3-, or 4-hydroxyphenyl, 2,-3-, or 4-methoxyphenyl, 2, -3-, or 4-pyridylmethyl, benzyl, 2,-3-, or 4-hydroxybenzyl, 2,-3-, or 4-benzyloxybenzyl, 2,-3-, or 4-$C_1-C_6$ alkoxybenzyl, or benzyloxy ($C_1-C_6$ alkyl).

10. A compound as claimed in claim 2 wherein $R_3$ is $C_1-C_6$ alkyl, phenyl, 2,-3-, or 4-hydroxyphenyl, 2,-3-, or 4-methoxyphenyl, 2, -3-, or 4-pyridylmethyl, benzyl, 2,-3-, or 4-hydroxybenzyl, 2,-3-, or 4-benzyloxybenzyl, 2,-3-, or 4-$C_1$–$C_6$ alkoxybenzyl, or benzyloxy ($C_1$–$C_6$ alkyl).

11. A compound as claimed in claim 1 wherein $R_3$ is a characterizing group of a natural α amino acid, in which any functional group may be protected, any amino group may be acylated and any carboxyl group present may be amidated.

12. A compound as claimed in claim 2 wherein $R_3$ is a characterizing group of a natural α amino acid, in which any functional group may be protected, any amino group may be acylated and any carboxyl group present may be amidated.

13. A compound as claimed in claim 1 wherein $R_3$ is a benzyl group substituted in the phenyl ring by a group of formula —$OCH_2COR_8$ where $R_8$ is hydroxyl, amino, ($C_1$–$C_6$)alkoxy, phenyl ($C_1$–$C_6$)alkoxy, ($C_1$–$C_6$)alkylamino, di(($C_1$–$C_6$)alkyl)amino, phenyl($C_1$–$C_6$)alkyl)amino, the residue of an acid halide or amino acid or ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid.

14. A compound as claimed in claim 2 wherein $R_3$ is a benzyl group substituted in the phenyl ring by a group of formula —$OCH_2COR_8$ where $R_8$ is hydroxyl, amino, ($C_1$–$C_6$)alkoxy, phenyl ($C_1$–$C_6$)alkoxy, ($C_1$–$C_6$)alkylamino, di(($C_1$–$C_6$)alkylamino, phenyl($C_1$–$C_6$)alkyl) amino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid.

15. A compound as claimed in claim 1 wherein $R_3$ is a heterocyclic ($C_1$–$C_6$)alkyl group, either being unsubstituted or mono- or di-substituted in the heterocyclic ring with halo, nitro, carboxy, ($C_1$–$C_6$)alkoxy, cyano ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$) alkyl or ($C_1$–$C_6$)alkylphenylmethyl.

16. A compound as claimed in claim 2 wherein $R_3$ is a heterocyclic ($C_1$–$C_6$)alkyl group, either being unsubstituted or mono- or di-substituted in the heterocyclic ring with halo, nitro, carboxy, ($C_1$–$C_6$)alkoxy, cyano ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$) alkyl or ($C_1$–$C_6$)alkylphenylmethyl.

17. A compound as claimed in claim 1 wherein $R_3$ is a group —$CR_aR_bR_c$ in which:
   each of $R_a$, $R_b$ and $R_c$ is independently hydrogen, ($C_1$–$C_6$) alkyl, ($C_2$–$C_6$)alkenyl, ($C_1$–$C_6$)alkynyl, phenyl($C_1$–$C_6$) alkyl, ($C_3$–$C_8$)cycloalkyl; or
   $R_c$ is hydrogen and $R_a$ and $R_b$ are independently phenyl or heteroaryl or
   $R_c$ is hydrogen, ($C_1$–$C_6$)alkyl, ($C_2$–$C_6$)alkenyl, phenyl ($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or
   $R_a$, $R_b$ and $R_c$ together with the carbon atom to which they are attached form a tricyclic ring; or
   $R_a$ and $R_b$ are each independently ($C_1$–$C_6$)alkyl, ($C_2$–$C_6$) alkyl, ($C_2$–$C_6$)alkenyl, ($C_1$–$C_6$)alkynyl, phenyl ($C_1$–$C_6$)alkyl, or a group as defined for $R_c$ below other than hydrogen, or
   $R_a$ and $R_b$ together with the carbon atom to which they are attached form a cycloalkyl or heterocyclic ring, and $R_c$ is hydrogen, —OH, —SH, halogen, —CN, —$CO_2H$, ($C_1$–$C_4$)perfluoroalkyl, —$CH_2OH$, —$CO_2$($C_1$–$C_6$) alkyl, —O($C_2$–$C_6$)alkenyl, —S(($C_1$–$C_6$)alkyl, SO($C_1$–$C_6$)alkyl, —O($C_1$–$C_6$)alkyl, —$SO_2$($C_1$–$C_6$) alkyl, —S($C_2$–$C_6$)alkenyl, —SO($C_2$–$C_6$)alkenyl, —$SO_2$($C_2$–$C_6$)alkenyl or a group —Q—W wherein Q represents a bond or —O—, S—, —SO—, or —$SO_2$— and W represents a phenyl, phenylalkyl, ($C_3$–$C_8$) cycloalkyl, ($C_1$–$C_8$)cycloalkylalkyl, ($C_4$–$C_8$) cycloalkenyl ($C_4$–$C_8$)cycloalkenyl, ($C_4$–$C_8$) cycloalkenylalkyl, heteroaryl or heteroarylalkyl group, which group W is optionally substituted by one or more substituents independently selected from the group consisting of hydroxyl, halogen, —CN, —$CO_2H$, —$CO_2$($C_1$–$C_6$)alkyl, —$CONH_2$, —CONH($C_1$–$C_6$) alkyl, —CONH($C_1$–$C_6$alkyl)$_2$, —CHO, —$CH_2OH$, ($C_1$–$C_4$)perfluoroalkyl, —O($C_1$–$C_6$)alkyl, —S($C_1$–$C_6$) alkyl, —SO($C_1$–$C_6$)alkyl, —$SO_2$($C_1$–$C_6$)alkyl, —$NO_2$, —$NH_2$, —NH($C_1$–$C_6$)alkyl, —N(($C_1$–$C_6$)alkyl, —$SO_2$ ($C_1$–$C_6$)alkmyl, —$NO_2$, —$NH_2$—NH($C_1$–$C_6$)alkyl, —N(($C_1$–$C_6$)alkyl)$_2$, —NNHCO($C_1$–$C_6$)alkyl, ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl and benzyl.

18. A compound as claimed in claim 2 wherein $R_3$ is a group —$CR_aR_bR_c$ in which:
   each of $R_a$, $R_b$ and $R_c$ is independently hydrogen, ($C_1$–$C_6$) alkyl, ($C_2$–$C_6$)alkenyl, ($C_1$–$C_6$)alkynyl, phenyl($C_1$–$C_6$) alkyl, ($C_3$–$C_8$)cycloalkyl; or
   $R_c$ is hydrogen and $R_a$ and $R_b$ are independently phenyl or heteroaryl or
   $R_c$ is hydrogen, ($C_1$–$C_6$)alkyl, ($C_2$–$C_6$)alkenyl, phenyl ($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or
   $R_a$, $R_b$ and $R_c$ together with the carbon atom to which they are attached form a tricyclic ring; or
   $R_a$ and $R_b$ are each independently ($C_1$–$C_6$)alkyl, ($C_2$–$C_6$) alkenyl, ($C_1$–$C_6$)alkynyl, phenyl ($C_1$–$C_6$)alkyl, or a group as defined for $R_c$ below other than hydrogen, or
   $R_a$ and $R_b$ together with the carbon atom to which they are attached form a cycloalkyl or heterocyclic ring, and $R_c$ is hydrogen, —OH, —SH, halogen, —CN, —$CO_2H$, ($C_1$–$C_4$)perfluoroalkyl, —$CH_2OH$, —$CO_2$($C_1$–$C_6$) alkyl, —O($C_2$–$C_6$)alkenyl, —S(($C_1$–$C_6$)alkyl, SO($C_1$–$C_6$)alkyl, —O($C_1$–$C_6$)alkyl, —$SO_2$($C_1$–$C_6$) alkyl, —S($C_2$–$C_6$)alkenyl, —SO($C_2$–$C_6$)alkenyl, —$SO_2$($C_2$–$C_6$)alkenyl or a group —Q—W wherein Q represents a bond or —O—, —S—, —SO—, or —$SO_2$— and W represents a phenyl, phenylalkyl, ($C_3$–$C_8$)cycloalkyl, ($C_1$–$C_8$)cycloalkylalkyl, ($C_4$–$C_8$) cycloalkenyl, ($C_4$–$C_8$)cycloalkenylalkyl, heteroaryl or heteroarylalkyl group, which group W is optionally substituted by one or more substituents independently, selected from the group consisting of hydroxyl, halogen, —CN, —$CO_2H$, —$CO_2$($C_1$–$C_6$)alkyl, $CONH_2$, —CONH($C_1$–$C_6$)alkyl, —CONH ($C_1$–$C_6$alkyl)$_2$, —CHO, —$CH_2OH$, ($C_1$–$C_4$) perfluoroalkyl, —O($C_1$–$C_6$)alkyl, —S($C_1$–$C_6$)alkyl, —SO($C_1$–$C_6$)alkyl, —$SO_2$($C_1$–$C_6$)alkyl, —$NO_2$, —$NH_2$, —N($C_1$–$C_6$)alkyl, —N(($C_1$–$C_6$)alkyl, —$SO_2$

53

(C₁–C₆)alkmyl, —NO₂, —NH₂—NH(C₁–C₆)alkyl, —N((C₁–C₆)alkyl)₂, —NNHCO(C₁–C₆)alkyl, (C₁–C₆)alkyl, (C₂–C₆)alkenyl, (C₂–C₆)alkynyl, (C₃–C₈)cycloalkyl, (C₄–C₈)cycloalkenyl, phenyl and benzyl.

19. A compound as claimed in claim 1 wherein R₃ is phenyl, benzyl, tert-butoxymethyl or iso-butyl.

20. A compound as claimed in claim 2 wherein R₃ is phenyl, benzyl, tert-butoxymethyl or iso-butyl.

21. A compound as claimed in claim 1 wherein R₄ is a group of formula —(C=O)OR₉ wherein R₉ is methyl, ethyl, n- or iso-propyl, n-, sec- or tert-butyl, 1-ethyl-prop-1-yl, 1-methyl-prop-1-yl, 1-methyl-but-1-yl, cyclopentyl, cyclohexyl, allyl, phenyl, benzyl, 2-, 3- or 4-pyridylmethyl, N-methylpiperidin-4-yl, 1-methylcyclopent-1-yl, adamantyl, tetrahydrofuran-3-yl or methoxyethyl.

22. A compound as claimed in claim 2 wherein R₄ is a group of formula —(C=O)OR₉ wherein R₉ is methyl, ethyl, n- or iso-propyl, n-, sec- or tert-butyl, 1-ethyl-prop-1yl, 1-methyl-prop-1-yl, 1-methyl-but-1-yl, cyclopentyl, cyclohexyl, allyl, phenyl, benzyl, 2-,3- or 4-pyridylmethyl, N-methylpiperidin-4-yl, 1-methylcyclopent-1yl, adamantyl, tetrahydrofuran-3-yl or methoxyethyl.

23. A compound as claimed in claim 1 wherein R₄ is a group of formula —(C=O)OR₉ wherein R₉ is benzyl, cyclopentyl, isopropyl or tert-butyl.

24. A compound as claimed in claim 2 wherein R₄ is a group of formula —(C=O)OR₉ wherein R₉ is benzyl, cyclopentyl, isopropyl or tert-butyl.

25. A compound as claimed in claim 1 wherein R is hydrogen or methyl.

26. A compound as claimed in claim 2 wherein R is hydrogen or methyl.

27. A compound as claimed in claim 1 wherein R₁ is n-propyl, allyl, methoxy or thienylsulfanyl-methyl, R₂ is isobutyl, n-hexyl, or 3-(2-chlorophenyl)prop-2-yn-1-yl, R₃ is phenyl, benzyl, tert-butoxymethyl or iso-butyl, R₄ is a group of formula —(C=O)OR₉ wherein R₉ is benzyl, cyclopentyl, isopropyl or tert-butyl and R is hydrogen or methyl.

28. A compound as claimed in claim 2 wherein R₁ is n-propyl, allyl, methoxy or thienylsulfanyl-methyl, R₂ is isobutyl, n-hexyl, or 3-(2-chlorophenyl)prop-2yn-1-yl, R₃ is phenyl, benzyl, tert-butoxymethyl or iso-butyl, R₄ is a group of formula —(C=))OR₉ wherein R₉ is benzyl, cyclopentyl, isopropyl or tert-butyl and R is hydrogen or methyl.

29. A composition, useful for inhibiting proliferation of tumor cells in mammals, comprising a compound as claimed in claim 1 together with a pharmaceutically acceptable carrier.

30. A composition, useful for inhibiting proliferation of tumor cells in mammals, comprising a compound as claimed in claim 2 together with a an acceptable carrier.

31. A compound of formula (I)

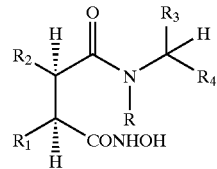

(I)

wherein R₁ is n-propyl, allyl, methoxy, ethoxy or hydroxy; R₂ is isobutyl; R₃ is phenyl; R₄ is a group of formula —(C=O)OR₆ wherein R₆ is cyclopentyl or cyclohexyl; R is hydrogen; and the stereochemical configuration of the car-

54 bon atom carrying the groups R₃ and R₄ is S; or a pharmaceutically acceptable salt, hydrate or solvate thereof.

32. The compound of claim 1, wherein said compound is 2S-(3S-Hydroxycarbamoyl-2R-isobutyl-hex-5-enoylamino)-2-phenylethanoic acid cyclopentyl ester, or a pharmaceutically acceptable salt, hydrate or solvate thereof.

33. A composition comprising a compound as claimed in claim 31 together with an acceptable carrier.

34. A composition comprising a compound as claimed in claim 32 together with an acceptable carrier.

35. A compound as claimed in claim 1 wherein R₁ is:

hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or C₁–C₄ alkyl, substituted by a moiety selected from the group consisting of phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo(1,2a)(1,2,4)-triazol-2-yl, or a naphthylimido, 1,3-dihydro-1-oxo-2H-benz(f)isoindol-2-yl, 1,3-dihydro-1,3-dioxo-2H-pyrrolo quinolin-2,3-dihydro-1,3-dioxo-1H-benz(d,e)isoquinolin-2-yl cyclohexyl, cyclooctyl, cycloheptyl, cyclopentyl, cyclobutyl, cyclopropyl, tetrahydropyranyl and morpholinyl.

36. The compound of claim 35, wherein the naphthylimido is 1,3-dihydro-1,3-dioxo-2H-benz(f)isoindol-2-yl.

37. A compound as claimed in claim 2 wherein R₁ is:

hydrogen, methyl, ethyl, n-propyl, n-butyl, isobutyl, hydroxyl, methoxy, allyl, phenylpropyl, phenylprop-2-enyl, thienylsulphanylmethyl, thienylsulphinylmethyl, or thienylsulphonylmethyl; or C₁–C₄ alkyl, substituted by a moiety selected from the group consisting of phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo(1,2a)(1,2,4)-triazol-2-yl, or a naphthylimido, 1,3-dihydro-1-oxo-2H-benz(f)isoindol-2-yl, 1,3-dihydro-1,3-dioxo-2H-pyrrolo(3,4-b)quinolin-2,3-dihydro-1,3-dioxo-1H-benz(d,e)isoquinolin-2-yl cyclohexyl, cyclooctyl, cycloheptyl, cyclopentyl, cyclobutyl, cyclopropyl, tetrahydropyranyl and morphholinyl.

38. The compound of claim 37, wherein the naphthylimido is 1,3-dihydro-1,3-dioxo-2H-benz(f)isoindol-2-yl.

39. A compound as claimed in 1 wherein R₂ is:

methyl, ethyl, n- or iso-propyl, n-, iso- or tert-butyl, n-pentyl, n-hexyl, n-heptyl, n-nonyl, n-decyl, prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl, 3-(4-pridyl)phenyl)prop-2-yn-1-yl, 3-(4-phenylphenyl)propyl, 3-(4-phenyl)phenyl)prop-2-yn-1-yl or 3-((4-chlorophenyl)phenyl)propyl.

40. A compound as claimed in 2 wherein $R_2$ is:

methyl, ethyl, n- or iso-propyl, n-, iso- or tert-butyl, n-pentyl, n-hexyl, n-heptyl, n-nonyl, n-decyl, prop-2-yn-1-yl, phenylpropyl, 4-chlorophenylpropyl, 4-methylphenylpropyl, 4-methoxyphenylpropyl, phenoxybutyl, 3-(4-pyridylphenyl)propyl, 3-(4-pridyl)phenyl)prop-2-yn-1-yl, 3-(4-phenylphenyl)propyl, 3-(4-phenyl)phenyl)prop-2-yn-1-yl or 3-((4-chlorophenyl)phenyl)propyl.

41. A compound as claimed in claim 1 wherein $R_3$ is a group —(Alk)$_n$R$_6$ where Alk is a ($C_1$–$C_6$) alkyl or ($C_2$–$C_6$) alkenyl group optionally interrupted by one or more —O—, or —S— atoms or —N($R_7$)— groups where $R_7$ is a hydrogen atom or a ($C_1$–$C_6$)alkyl group, n is 0 or 1, and $R_6$ is an optionally substituted cycloalkyl or cycloalkenyl group.

42. A compound as claimed in claim 2 wherein $R_3$ is a group —$_n$R$_6$ where Alk is a ($C_1$–$C_6$) alkyl or ($C_2$–$C_6$)alkenyl group optionally interrupted by one or more —O—, or —S— atoms or —N($R_7$)— groups where $R_7$ is a hydrogen atom or a ($C_1$–$C_6$)alkyl group, n is 0 or 1, and $R_6$ is an optionally substituted cycloalkyl or cycloalkenyl group.

43. A compound as claimed in claim 2 selected from the group consisting of 2S-(3S-Hydroxycarbamoyl-2R-isobutyl-hex-5-enoylamino)-3-phenylpropionic acid cyclopentyl ester, 2S-(3S-Hydroxycarbamoyl-2R-isobutyl-hex-5-enoylamino)-3-phenylpropionic acid benzyl ester, 2S-(2R-(1S-Hydroxycarbamoyl-2-(thiophen-2-ylsulphanyl)-ethyl)-4-methyl-pentanoylamino)-3-phenyl-propionic acid isopropyl ester, 2S-(3S-Hydroxycarbamoyl-2R-isobutyl-hex-5-enoylamino)-4-methyl-pentanoic acid cyclopentyl ester, and pharmaceutically acceptable salts, hydrates and esters thereof.

44. A compound as claimed in claim 2 selected from the group consisting of 2S-(3S-Hydroxycarbamoyl-2R-isobutyl-hex-5-enoylamino)-3-phenylpropionic acid methyl ester, 2S-(3S-Hydroxycarbamoyl-2R-isobutyl-hex-5-enoylamino)-3-phenylpropionic acid ethyl ester, 2S-(3S-Hydroxycarbamoyl-2R-isobutyl-hex-5-enoylamino)-3-phenylpropionic acid isopropyl ester, 3R-(2-Phenyl-1S methylcarboxy-ethylcarbamoyl)-2S,5-dimethylhexanohydroxamic acid, 2S-(3S-Hydroxycarbamoyl-2R-isobutyl-hex-5-enoylamino)-3-phenyl-propionic acid tert-butyl ester, 2S-(2R-Hydroxycarbamoylmethyl-4-methyl-pentanoylamino)-3-phenyl-propionic acid isopropyl ester, 2S-(2R-Hydroxy-hydroxycarbamoyl-methyl)-4-methyl-pentanoylamine)-3-phenyl-propionic acid isopropyl ester, 2S-(2R-(1S-Hydroxycarbamoyl-ethyl)-4-methyl-pentanoylamino)-3-phenyl-propionic acid isopropyl ester, 2S-(2R-Hydroxycarbamoylmethyl-octanoylamino)-3-phenyl-propionic acid isopropyl ester, 2S-(2R-(S-Hydroxy-hydroxycarbamoyl-methyl)-4-methyl-pentanoylamino)-3-phenyl-propionic acid cyclopentyl ester, 2S-(3S-Hydroxycarbamoyl-2R-isobutyl-hex-5-enoylamino)-3S-methyl-pentanoic acid cyclopentyl ester, 2S-(3S-Hydroxycarbamoyl-2R-isobutyl-hex-5-enoylamino)-3S-methyl-pentanoic acid cyclopentyl ester, 2S-(3S-Hydroxycarbamoyl-2R-isobutyl-hex-5-enoylamino)-3-phenylpropionic acid 2-methoxy-ethyl ester, 2S-(2R-(1S-Hydroxycarbamoyl-ethyl)-4-methyl-pentanoylamino)-3-phenyl-propionic acid 2-methoxy-ethyl ester, 2S-(3S-Hydroxycarbamoyl-2R-isobutyl-hexanoylamino)-3,3-dimethyl-butyric acid 2-methoxy-ethyl ester, 2S-(2R-(S-Hydroxycarbamoyl-methoxy-methyl)-4-methyl-pentanoylamino)-3-phenyl-propionic acid isopropyl ester, 2S-(2-R-(1S-Hydroxycarbamoyl-ethyl)-4-methyl-pentanoylamino)-3,3-dimethyl-butyric acid 2-methoxy-ethyl ester, 2S-(3S-Hydroxycarbamoyl-2R-isobutyl-hex-5-enoylamino)(-3,3-dimethyl-butyric acid 2-methoxy-ethyl ester, 2S-(3S-Hydroxycarbamoyl-2R-isobutyl-hexanoylamino)-3-phenylpropionic acid isopropyl ester, 2S-(3S-Hydroxycarbamoyl-2R-isobutyl-hex-5-enoylamino)-3,3-dimethyl-butyric acid isopropyl ester, 2R-(3S-Hydroxycarbamoyl-2R-isobutyl-hex-5-enoylamino)-3-phenylpropionic acid isopropyl ester, 2S-(2R-(S-Hydroxy carbamoyl-methoxy-methyl)-4-methyl-pentanoylamino)-3,3-dimethyl-butyric acid isopropyl ester, 2S-(3S-Hydroxycarbamoyl-2R-isobutyl-hex-5-enoyl)-methyl-amino)-3-phenylpropionic acid isopropyl ester, 3-Cyclohexyl-2S-(3S-hydroxycarbamoyl-2R-isobutyl-hex-5-enoylamino)-propionic acid cyclopentyl ester, 2S-(3S-Hydroxycarbamoyl-2R-isobutyl-hex-5-enoylamino)-3-phenylpropionic acid 1-methyl-piperidin-4-yl ester, 2S-(3S-Hydroxycarbamoyl-2R-isobutyl-hex-5-enoylamino)-3-phenylpropionic acid 1-methyl-piperidin-4-yl ester, 2S-(3S-Hydroxycarbamoyl-2R-isobutyl-hex-5-enoylamino)-3-phenylpropionic acid 1-ethyl propyl ester, 2S-(3S-Hydroxycarbamoyl-2R-isobutyl-hex-5-enoylamino)-3-phenylpropionic acid 1S-methyl-butyl ester, 2S-(3S-Hydroxycarbamoyl-2R-isobutyl-hex-5-enoylamino)-3-phenylpropionic acid cyclohexyl ester, 2S(2R-(1S-Hydroxycarbamoyl-2-(thiophen-2-ylsulphanyl)-ethyl)-4-methyl-pentanoylamino)-3,3-dimethyl-butyric acid isopropyl ester, 2S-(3S-Hydroxycarbamoyl-2R-isobutyl-hex-5-enoylamino)-3-phenylpropionic acid 1R-methyl-butyl ester, 2S-(3S-Hydroxycarbamoyl-2R-isobutyl-hex-5-enoylamino)-3-phenylpropionic acid tetrahydro-furan-3(R,S)-yl ester, 2S-(3S-Hydroxycarbamoyl-2R-isobutyl-hex-5-enoylamino)-3,3-dimethyl-butyric acid cyclopentyl ester, 2S-(2R-(1S-Cyclopentyl-hydroxycarbamoyl-methyl)-4-methyl-pentanoylamino)-3-phenyl-propionic acid cyclopentyl ester, 2S-(2R-(1S-Hydroxy-hydroxycarbamoyl-methyl)-pent-4-ynoylamino)-3-phenylpropionic acid cyclopentyl ester, 2S-(3S-Hydroxycarbamoyl-2R-isobutyl-hex-5-enoylamino)-3-pyridin-3-yl-propionic acid cyclopentyl ester, 3-tert-Butoxy-2S-(3S-hydroxycarbamoyl-2R-isobutyl-hex-5-enoylamino)-propionic acid cyclopentyl ester, 2S-(5-(2-Chlorophenyl)-2R-(1S-hydroxy-hydroxycarbamoyl-methyl)-pent-4-ynoylamino)-3-phenylpropionic acid cyclopentyl ester, 2S-(3S-Hydroxycarbamoyl-2R-isobutyl-6-phenyl-hex-5-enoylamino)-3-phenyl-propionic acid cyclopentyl ester, and pharmaceutically acceptable salts, hydrates and esters thereof.

45. A composition comprising a compound as claimed on claim 44 together with an acceptable carrier.

46. A composition comprising a compound as claimed in claim 45 together with an acceptable carrier.

* * * * *